United States Patent [19]
Funaki et al.

[11] Patent Number: 6,153,794
[45] Date of Patent: Nov. 28, 2000

[54] PHOSPHINE SULFIDE, A MANUFACTURING PROCESS THEREFOR AND USE THEREOF

[75] Inventors: Katsuhiko Funaki; Isao Hara; Takaomi Hayashi; Shinji Kiyono; Atsushi Shibahara; Kazumi Mizutani; Tadahito Nobori, all of Kanagawa; Usaji Takaki, Fujisawa, all of Japan

[73] Assignee: Mitsui Chemicals, Inc., Japan

[21] Appl. No.: 09/348,586

[22] Filed: Jul. 7, 1999

[30] Foreign Application Priority Data

Jul. 15, 1998 [JP] Japan .................................. 10-200858
Dec. 17, 1998 [JP] Japan .................................. 10-359517

[51] Int. Cl.$^7$ .............................. C07F 9/22; C07C 43/11; C07C 69/76
[52] U.S. Cl. ........................... 564/14; 568/606; 568/613; 568/618; 564/15; 560/55
[58] Field of Search ................................ 564/12, 14, 15; 568/606, 613, 618; 560/55, 57, 61

[56] References Cited

U.S. PATENT DOCUMENTS 5,232,895  8/1993  Broadhurst et al. .................... 504/200
5,360,563  11/1994  Zinke et al. ........................... 252/46.7

FOREIGN PATENT DOCUMENTS 0763555A  3/1997  European Pat. Off. .
791600  8/1997  European Pat. Off. .

OTHER PUBLICATIONS

Koidan G. N. et al, "Methylation of the phosphoryl group by methyl iodide", Journal of General Chemistry of the USSR, vol. 55, No. 7, p. 1453, Oct., 1985.

Esswein B. et al, "Use of polyiminophosphazene bases for ring–opening polymerizations", Macromolecular Symposia, vol. 107, pp. 331–340, Apr. 1996.

Esswein B. et al, "Anionic polymerization of oxirane in the presence of the polyiminophosphazene base T–Bu–P4", Macromolecular Rapid Communications, vol. 17, pp. 143–148, 1996.

*Primary Examiner*—Jean F Vollano
*Attorney, Agent, or Firm*—Burns, Doane, Swecker, and Mathis, L.L.P.

[57] ABSTRACT

An organic compound which is basic and soluble in an organic solvent, does not have a problem in preparation or handling and exhibits catalytic activity as a basic compound, i.e., a phosphine sulfide represented by formula (1), and a manufacturing process therefor, i.e., manufacturing a phosphine sulfide represented by formula (1), by reacting one molecule of thiophosphoryl chloride with three molecules of a phosphorane represented by formula (2). The phosphine sulfide can be used in a process for effectively manufacturing a poly(alkylene oxide) by polymerizing an alkylene oxide in the presence of the phosphine sulfide or of the phosphine sulfide and an active hydrogen compound selected from water and organic compounds having a partial structure of —OH or —NH—; and 2) a process for manufacturing a 1,2-dioxyethane derivative from an epoxy compound, i.e, manufacturing a 1,2-dioxyethane derivative by reacting an epoxy compound with a carboxylate, carboxylic anhydride, carbonate or phenol compound, respectively, in the presence of the phosphine sulfide.

20 Claims, 3 Drawing Sheets

PHOSPHINE SULFIDE, A MANUFACTURING PROCESS THEREFOR AND USE THEREOF

BACKGROUND OF THE INVENTION

1. Field of the Invention

This invention relates to a novel and useful phosphine sulfide represented by formula (1) and a manufacturing process therefor.

This invention also relates to a process for manufacturing a poly(alkylene oxide) by polymerizing an alkylene oxide in the presence of the phosphine sulfide.

A poly(alkylene oxide) is an important polymer, for example, as a starting material for a polyurethane foam or elastomer by reacting it with an isocyanate or as a surfactant.

This invention also relates to a process for manufacturing a 1,2-dioxyethane derivative by reacting an epoxy compound with a carboxylate, carboxylic anhydride, carbonate or phenol compound in the presence of the phosphine sulfide. Such a 1,2-dioxyethane derivative is a very important compound as an intermediate for a pesticide or medical drug or a starting compound for a polymer material.

2. Description of the Related Art

Hydroxides or carbonates of alkali or alkaline earth metals have been used as a catalyst or reagent for a variety of reactions because of their basicity. These are, however, water-soluble while generally insoluble in an organic solvent, and are, therefore, little applicable to a reaction in an organic solvent. Thus, there have been disclosed a variety of highly basic organic compounds such as 1,8-diazabicyclo[5.4.0]-7-undecene, 1,5-diazabicyclo(4.3.0)-5-nonene and 1,4-diazabicyclo[2.2.2]octane.

Their basicity or catalytic action based on their basicity are, however, limited. Recently, there have been found organic compounds designated as a phosphazene base consisting of carbon, hydrogen, nitrogen and phosphorous atoms which are strong bases having strong hydrogen-withdrawing ability (Nachr.Chem.Tech.Lab., 38, 1214–1226 (1990)).

It has been described that a phosphazene base may act as an effective catalyst for anionic polymerization of ethylene oxide using an alcohol as an initiator (Martin Moller et al., Macromol.Rapid Commun., 17, 143–148 (1996)).

A complicated process should be employed for preparing a phosphazene base, and in the process, a stronger base such as potassium amide should be used for making the phosphazene base strongly basic(Nachr.Chem.Tech.Lab., 38, 1216 (1990)). Preparation of a phosphazene base is, therefore, not industrially advantageous. In addition, the base has a problem in handling that it is susceptible to deterioration by carbon dioxide in the air due to its strong basicity.

Tris[tris(dimethylamino)phosphoranylideneamino] phosphine oxide is also known as a useful base (G. N. Koidan et al., Journal of General Chemistry of the USSR, 55, 1453 (1985)). The phosphine oxide is, however, extremely hygroscopic; for example, it may absorb moisture to 7 to 8 wt % after storing in an ordinary atmosphere (temperature: 18 to 24° C.; humidity: 52 to 59%) for 24 hours. Its solubility in water is 50 wt % or higher. Due to its higher hygroscopicity, the phosphine oxide can be used in limited applications as a catalyst and requires special precautions in handling for ensuring stable catalytic action.

For preparing a poly(alkylene oxide) by polymerization of an alkylene oxide, it is common to form an alkali-metal salt of an active hydrogen compound from an active hydrogen compound such as a polyhydric alcohol and a basic alkali-metal compound such as potassium hydroxide, by dehydration before initiation of polymerization. The process has been industrially put to practical use.

Initiator systems of other combinations have been disclosed. For example, U.S. Pat. No. 3,829,505 has disclosed preparation of a polymer of propylene oxide using a compound represented by $Zn_3[Fe(CN)_6]_2 \cdot H_2O \cdot dioxane$ as an active hydrogen compound. JP-A 2-276821 has disclosed preparation of a polymer by reacting a polyol prepared using zinc-hexacyanocobaltate complex with sodium methoxide and then with ethylene oxide. JP-A 62-232433 has disclosed preparation of a polymer by polymerizing ethylene oxide using a product which is prepared by adding a solution of diethylzinc in hexane to a dispersion of 1,4-butanediol and a nonionic surfactant in a slurry of fumed silica in hexane. Any of these, however, comprises a metal component. If there remains the metal component in a poly(alkylene oxide) product, it may adversely affect a reaction during preparation of polyurethane or the physical properties of polyurethane. Thus, a special procedure or complicated process is required for adequately removing the metal component in preparing the poly(alkylene oxide).

On the other hand, JP-A 50-159595 has disclosed preparation of a polymer from ethylene oxide, using an initiator system which is a combination of an alkanepolyol as an active hydrogen compound and boron trifluoride-etherate. It is, however, known for the initiator system that a specific impurity in the polymer may adversely affect physical properties of polyurethane and thus a complicated process is required to adequately remove it. JP-A 57-12026 has disclosed preparation of a polymer of an alkylene oxide using an alcohol and aminophenol. JP-A 56-38323 has disclosed polymerization of propylene oxide using sorbitol and tetramethylammonium hydroxide. These systems, however, have problems such as insufficient polymerization activity and residual amine odor.

A process for preparing a poly(alkylene oxide) is known, in which an alkylene oxide is polymerized in the presence of a phosphazene base and an active hydrogen compound (EP 0763555; Macromol.Rapid Commun., Vol.17, pp.143–148 (1996); Macromol.Symp., Vol.107, pp.331–340 (1996)). The phosphazene base in the process is an initiator having a strong basicity. A complicated process should be, however, employed for preparing the phosphazene base, and in the process, a stronger base such as potassium amide should be used for making the phosphazene base strongly basic. Preparation of a phosphazene base is, therefore, not industrially advantageous. In addition, the base has a problem in handling that it is susceptible to deterioration by carbon dioxide in the air due to its strong basicity.

EP 0791600 has disclosed a process for preparing a poly(alkylene oxide) by polymerizing an alkylene oxide in the presence of substantially a phosphazenium salt of an active hydrogen compound. In this process, prior to initiating polymerization, the phosphazenium salt of the active hydrogen compound should be prepared by, for example, dehydration as in the process using an active hydrogen compound and an alkali-metal hydroxide as an initiation system, or desalting, which requires an additional equipment. Furthermore, inorganic salts formed during the step may interfere with successful proceeding of the polymerization, and therefore, the salts should be removed, making the process more complicated. Thus, the process should be industrially improved.

It is known that for example tertiary amines, quaternary ammonium salts and quaternary phosphonium salts may enhance a reaction of an epoxy compound with a carboxylate, carboxylic anhydride or carbonate to prepare a 1,2-dioxyethane derivative (K.Funabashi, Bulletin Chemical Society of Japan, vol.52, p.1488 (1979); Tadaomi Nishikubo, Yuki Gosei Kyokai Shi, vol.49 (3), p.219 (1991)). However, such a catalyst as the tertiary amines, quaternary ammonium salts and quaternary phosphonium salts exhibits inadequate activity. The catalyst may be used in an increased amount or concentration or the reaction may be conducted under severe conditions, to adequately proceed the reaction, but such a manipulation may cause problems such as side reactions and decomposition of a reactant or product, and an yield or selectivity is inadequate.

It is also known that an acid such as boron trifluoride or a base such as a tertiary amine and a tertiary phosphine may accelerate a reaction of an epoxy compound and a phenol compound to prepare a 1,2-dioxyethane derivative. These conventional acid or base catalysts, however, have inadequate catalytic activity.

SUMMARY OF THE INVENTION

An object of this invention is to provide an organic compound which is basic and soluble in an organic solvent, does not have a problem in preparation or handling as described above and exhibits catalytic activity as a basic compound.

Another object of this invention is to provide a process for manufacturing the above compound.

Further object of this invention is to provide a process for effectively manufacturing a poly(alkylene oxide) by polymerizing an alkylene oxide in the presence of the above compound, which does not require any treatment prior to polymerization and does not generate residual amine odor.

Further object of this invention is to find a catalyst which is highly active for a reaction of an epoxy compound with a carboxylate, carboxylic anhydride, carbonate or phenol compound and to provide an effective process for manufacturing a 1,2-dioxyethane derivative using the catalyst in a higher yield.

We have intensely attempted to achieve these objects and finally have prepared a phosphine sulfide consisting of carbon, hydrogen, nitrogen, phosphorous and sulfur atoms represented by formula (1), which is suitable for solving the above problems.

The first aspect of this invention is a phosphine sulfide represented by formula (1):

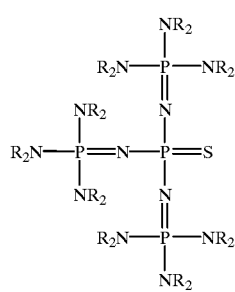

(1)

wherein R is the same or different and each represents a hydrocarbon group having 1 to 10 carbon atoms.

The second aspect of this invention is a process for manufacturing a phosphine sulfide represented by formula (1), comprising reacting one molecule of thiophosphoryl chloride with three molecules of a phosphorane represented by formula (2):

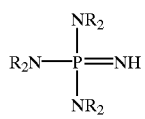

(2)

wherein R is the same or different and each represents a hydrocarbon group having 1 to 10 carbon atoms. "Reacting one molecule of thiophosphoryl chloride with three molecules of a phosphorane represented by formula (2)" indicates stoichiometry that three chlorine atoms in the thiophosphoryl chloride are replaced with the phosphorane; thus it does not indicate the ratio of quantity between them in a practical manufacturing reaction.

The third aspect of this invention is a process for manufacturing a poly(alkylene oxide), comprising polymerizing an alkylene oxide in the presence of a phosphine sulfide represented by formula (1) or of the phosphine sulfide and an active hydrogen compound selected from water and organic compounds having a partial structure of —OH or —NH—.

The fourth aspect of this invention is a process for manufacturing a 1,2-dioxyethane derivative having a partial structure represented by formula (3), (4), (5) or (6):

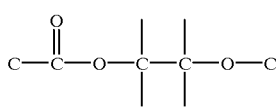

(3)

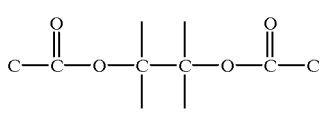

(4)

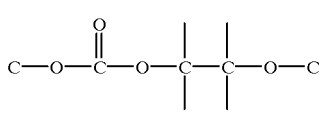

(5)

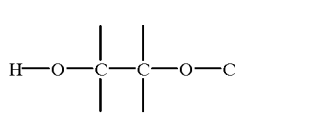

(6)

wherein a carbon atom C— or —C attached to a carbonyl group or an oxygen atom belongs to an aliphatic, alicyclic or aromatic hydrocarbon, comprising reacting an epoxy compound with a carboxylate, carboxylic anhydride, carbonate or phenol compound, respectively, in the presence of a phosphine sulfide represented by formula (1).

DESCRIPTION OF THE PREFERRED EMBODIMENTS

Figure 1:
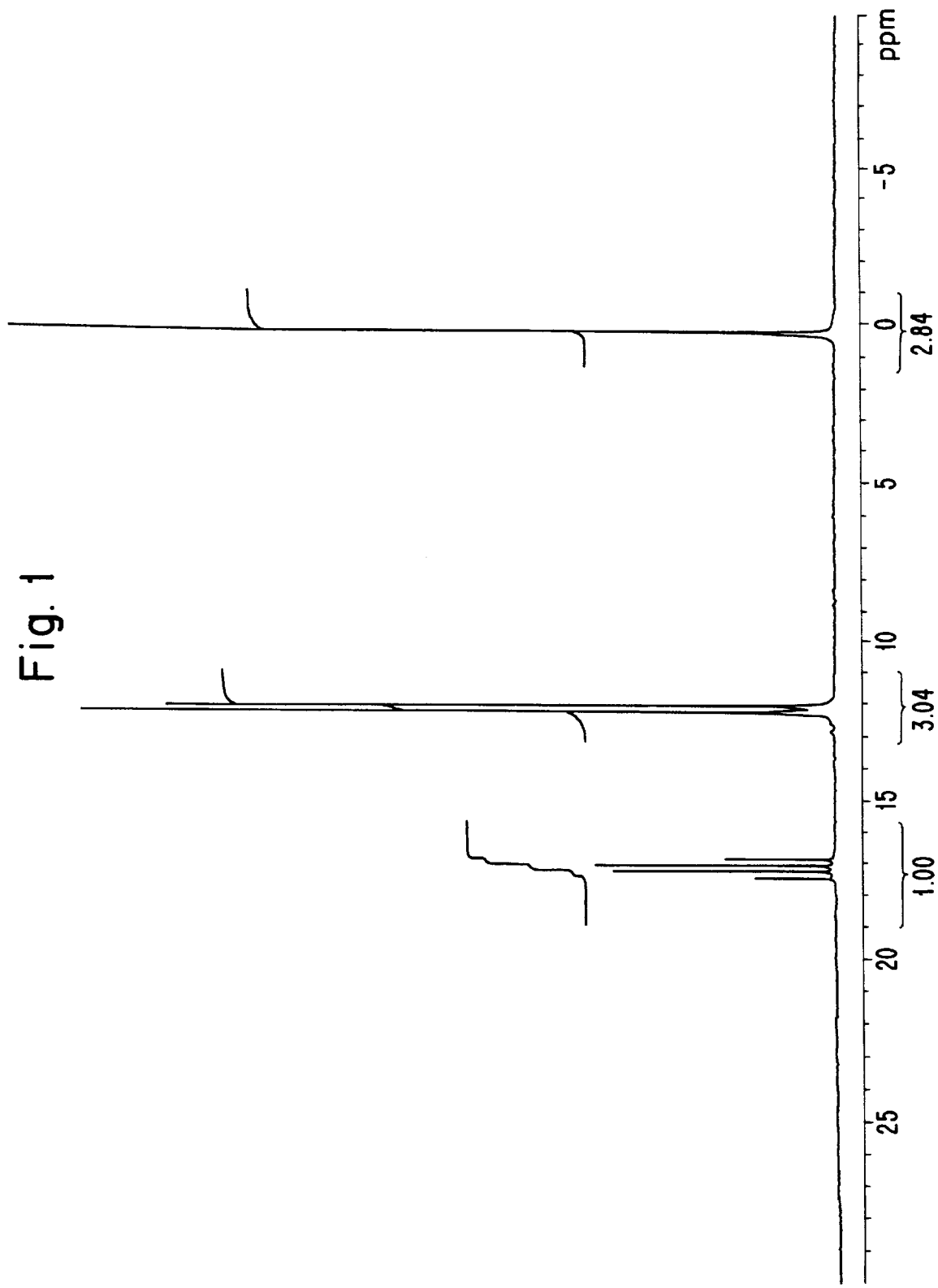
FIG. 1 shows a $^{31}$P-NMR spectrum for tris [tris (dimethylamino)phosphoranylideneamino]phosphine sulfide (solvent: DMSO-$d_6$).

Formula (1) is a limiting structure for a phosphine sulfide in this invention, where phosphorous and sulfur atoms are bound via a double bond, but alternatively, the compound may have a limiting structure where electrons are localized on the sulfur atom to form an anion while the phosphorous has a cationic form, i.e., $P^+$—$S^-$. The positive charge on the phosphorous atom may be delocalized over the molecule via a conjugated system. It should be, therefore, noted that the phosphine sulfide represented by formula (1) is a resonance hybrid including all the limiting structures.

The first and the second aspects of this invention will be described. R in the phosphine sulfide represented by formula (1) is the same or different and each represents a hydrocarbon group having 1 to 10 carbon atoms, including, aliphatic, alicyclic and aromatic hydrocarbon groups such as methyl, ethyl, n-propyl, isopropyl, allyl, n-butyl, sec-butyl, tert-butyl, 2-butenyl, 1-pentyl, 2-pentyl, 3-pentyl, 2-methyl-1-butyl, isopentyl, tert-pentyl, 3-methyl-2-butyl, neopentyl, n-hexyl, 4-methyl-2-pentyl, cyclopentyl, cyclohexyl, 1-heptyl, 3-heptyl, 1-octyl, 2-octyl, 2-ethyl-1-hexyl, 1,1-dimethyl-3,3-dimethylbutyl (commonly, tert-octyl), nonyl, decyl, phenyl, 4-tolyl, benzyl, 1-phenylethyl and 2-phenylethyl. Alternatively, two Rs attached to the same nitrogen atom may be linked together to form a ring structure.

R is preferably methyl, ethyl or n-propyl, more preferably methyl.

The phosphine sulfide represented by formula (1) is a novel and unknown compound, and a manufacturing process therefor or its catalytic action has not been, of course, indicated or suggested in any known literature.

The phosphine sulfide represented by formula (1) may be prepared by reacting one molecule of thiophosphoryl chloride with three molecules of a phosphorane represented by formula (2). The reaction can be represented by equation (7):

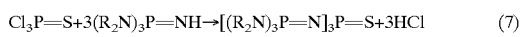

$$Cl_3P{=}S + 3(R_2N)_3P{=}NH \rightarrow [(R_2N)_3P{=}N]_3P{=}S + 3HCl \quad (7)$$

In this preparation process, the practical amount of the phosphorane represented by formula (2) to one mole of thiophosphoryl chloride is generally at least 3 moles, preferably 3 to 20 moles, more preferably 6 to 8 moles. Another basic compound may be present as a receptor for hydrogen chloride, a by-product of the reaction. Alternatively, 6 moles or more of the phosphorane may be present to use the excessive phosphorane as a hydrogen chloride receptor, where the phosphorane after receiving hydrogen chloride takes a form of phosphonium chloride, $(R_2N)_3P^+(NH_2)Cl^-$.

A reaction temperature may be generally −30 to 250° C., preferably 0 to 200° C., more preferably 20 to 150° C. The reaction temperature may be stepwise graded; for example, a lower temperature in an initial stage to an elevated temperature in the final stage. The reaction may be conducted under a reduced, atmospheric or increased pressure; generally under an atmospheric pressure.

A reaction duration may vary depending on various factors such as a reaction temperature, but is generally 0.1 to 100 hours, preferably 1 to 50 hours, more preferably 2 to 30 hours.

In the reaction, a solvent is generally used. Solvents which may be used include saturated aliphatic and saturated alicyclic hydrocarbons such as pentane, hexane, cyclohexane, heptane, octane, nonane and decane; unsubstituted or alkyl-substituted aromatic hydrocarbons such as benzene, toluene, o-xylene, m-xylene, p-xylene, ethylbenzene, n-propylbenzene, cumene, 1,2,3-trimethylbenzene, 1,2,4-trimethylbenzene, mesitylene, tetralin, butylbenzene, p-cymene, cyclohexylbenzene, 1,2-diethylbenzene, 1,3-diethylbenzene, 1,4-diethylbenzene, 1,2-diisopropylbenzene, 1,3-diisopropylbenzene, 1,4-diisopropylbenzene, 1,2,4-triethylbenzene, 1,3,5-triethylbenzene and dodecylbenzene; halogenated aromatic hydrocarbons such as chlorobenzene, o-dichlorobenzene, m-dichlorobenzene, 1,2,4-trichlorobenzene, bromobenzene, o-dibromobenzene, m-dibromobenzene, 1-bromo-2-chlorobenzene, 1-bromo-3-chlorobenzene, 1-bromonaphthalene and 1-chloronaphthalene; and halogenated alkyl-substituted aromatic hydrocarbons such as 2-chlorotoluene, 3-chlorotoluene, 4-chlorotoluene, 2-bromotoluene, 3-bromotoluene, 2,4-dichlorotoluene, 3,4-dichlorotoluene, 1-bromo-2-ethylbenzene, 1-bromo-4-ethylbenzene, 1-chloro-2-ethylbenzene, 1-chloro-4-ethylbenzene, 1-chloro-4-isopropylbenzene, 1-bromo-4-isopropylbenzene, mesityl chloride, 4-chloro-o-xylene and 2-chloro-o-xylene.

Any other solvent may be used as long as it does not adversely affect the process of this invention. Preferable solvents are alkyl-substituted aromatic hydrocarbons having 7 to 9 carbon atoms such as toluene, o-xylene, m-xylene, p-xylene, ethylbenzene and mesitylene; chlorinated benzenes having 1 to 3 chlorine atoms such as chlorobenzene, o-dichlorobenzene and 1,2,4-trichlorobenzene; and chlorinated alkyl-substituted aromatic hydrocarbons having 7 to 9 carbon atoms and 1 to 2 chlorine atoms such as 2-chlorotoluene, 2,4-dichlorotoluene, 1-chloro-4-ethylbenzene and mesityl chloride.

These solvents may be used alone or in combination of two or more. There are no limitations for the amount of the solvent, but it is generally below 500 wt parts, preferably 1 to 100 wt. parts, more preferably 1.5 to 20 wt. parts per wt. part of the starting material, thiophosphoryl chloride. It may be acceptable that liquid thiophosphoryl chloride is partially insoluble.

After the reaction, the phosphine sulfide represented by formula (1) which has been generated may be isolated by a common technique. For example, the above phosphonium chloride as a by-product is generally precipitated as a solid in the reaction solution. Thus, it may be removed by filtration, and then the filtrate may be washed with water. After evaporation of the solvent, the phosphine sulfide is isolated as a solid. A further purification technique such as recrystallization may be, if necessary, conducted.

Thus, phosphine sulfide represented by formula (1) can be prepared by a convenient process of this invention. The phosphine sulfide is soluble in non-polar to polar organic solvents. It has been surprisingly found that the phosphine oxide is not hygroscopic at all.

A hygroscopicity test for 48 hours under a ordinary atmosphere (temperature: 18 to 24° C.; humidity: 52 to 59%) has indicated no weight increase due to absorption of moisture for tris[tris(dimethylamino) phosphoranylideneamino]phosphine sulfide, a compound represented by formula (1) where R is methyl. The phosphine sulfide is considerably advantageous in its handling, in comparison with tris[tris(dimethylamino) phosphoranylideneamino]phosphine oxide which absorbs moisture in an amount of 7 to 8 wt % for 24 hours under the same conditions as described above. The phosphine sulfide is quite insoluble in water, but may provide a 0.003 M aqueous solution. The pH of the low-concentration aqueous solution is pH 11.25, indicating that the phosphine sulfide is basic.

The phosphine sulfide represented by formula (1) is very useful, for example, in a process for preparing a poly (alkylene oxide) by polymerizing an alkylene oxide or a process for preparing a 1,2-dioxyethane derivative by reacting an epoxy compound with a carboxylate, carboxylic anhydride, carbonate or phenol compound, as described later.

The third aspect of this invention will be described.

The third aspect of this invention is a process for manufacturing a poly(alkylene oxide), comprising polymerizing an alkylene oxide in the presence of a phosphine sulfide represented by formula (1) or of the phosphine sulfide and an active hydrogen compound selected from water and organic compounds having a partial structure of —OH or —NH—.

In the process of this invention, the phosphine sulfide represented by formula (1) may react with the alkylene oxide and/or the active hydrogen compound to form a derivative of the phosphine sulfide, which may act as an initiator. Use of such a derivative of the phosphine sulfide prepared in advance or separately, in the polymerization of the alkylene oxide, is encompassed in the concept of this invention that an alkylene oxide compound is polymerized in the presence of a phosphine sulfide represented by formula (1) or of the phosphine sulfide and an active hydrogen compound selected from water and organic compounds having a partial structure of —OH or —NH—.

An alkylene oxide in the process for manufacturing a poly(alkylene oxide) is a compound comprising a three-membered epoxy group such as ethylene oxide, propylene oxide, 1,2-butylene oxide, 2,3-butylene oxide, styrene oxide, cyclohexene oxide, epichlorohydrin, epibromohydrin, methyl glycidyl ether, allyl glycidyl ether and phenyl glycidyl ether. Any other alkylene oxide may be used as long as it does not adversely affect the process of this invention. These may be used in combination of two or more, where two or more alkylene oxides may be used simultaneously or sequentially or sequential use of these may be repeated.

The alkylene oxide is preferably ethylene oxide, propylene oxide, 1,2-butylene oxide or styrene oxide, more preferably ethylene oxide or propylene oxide, further preferably propylene oxide.

An active hydrogen compound in the process for manufacturing a poly(alkylene oxide) is a compound selected from water and organic compounds having a partial structure of —OH or —NH—.

It may be water. Organic compounds having a partial structure of —OH may include carboxylic acids having 1 to 20 carbon atoms such as formic acid, acetic acid, propionic acid, butyric acid, isobutyric acid, lauric acid, stearic acid, oleic acid, phenylacetic acid, dihydrocinnamic acid, cyclohexane carboxylic acid, benzoic acid, p-methylbenzoic acid and 2-carboxynaphthalene; polycarboxylic acids having 2 to 20 carbon atoms and 2 to 6 carboxyl groups such as oxalic acid, malonic acid, succinic acid, maleic acid, fumaric acid, adipic acid, itaconic acid, butane tetracarboxylic acid, phthalic acid, isophthalic acid, terephthalic acid, trimellitic acid and pyromellitic acid; carbamic acids such as N,N-diethylcarbamic acid, N-carboxypyrrolidone, N-carboxyaniline and N,N'-dicarboxy-2,4-toluenediamine; alcohols having 1 to 20 carbon atoms such as methanol, ethanol, n-propanol, isopropanol, n-butyl alcohol, sec-butyl alcohol, tert-butyl alcohol, iso-pentyl alcohol, tert-pentyl alcohol, n-octyl alcohol, lauryl alcohol, cetyl alcohol, cyclopentanol, cyclohexanol, allyl alcohol, crotyl alcohol, methyl vinyl carbinol, benzyl alcohol, 1-phenylethyl alcohol, triphenyl carbinol and cinnamyl alcohol; polyhydric alcohols having 2 to 20 carbon atoms and 2 to 8 hydroxyl groups such as ethylene glycol, propylene glycol, diethylene glycol, dipropylene glycol, 1,3-propanediol, 1,3-butanediol, 1,4-butanediol, 1,6-hexanediol, 1,4-cyclohexanediol, trimethylolpropane, glycerin, diglycerin, trimethylolmelamine, pentaerythritol and dipentaerythritol; saccharides and their derivatives such as glucose, sorbitol, dextrose, fructose and sucrose; aromatic compounds having 6 to 20 carbon atoms and 1 to 3 hydroxyl groups such as phenol, 2-naphthol, 2,6-dihydronaphthalene and bisphenol-A; and poly(alkylene oxide)s having 2 to 8 terminal ends and 1 to 8 hydroxyl groups at the terminal ends whose number-average molecular weight is 200 to 50,000, such as poly (ethylene oxide), poly(propylene oxide) and copolymers thereof.

Organic compounds having a partial structure of —NH— as an active hydrogen compound may include aliphatic and aromatic primary amines having 1 to 20 carbon atoms such as methylamine, ethylamine, n-propylamine, isopropylamine, n-butylamine, isobutylamine, sec-butylamine, tert-butylamine, cyclohexylamine, benzylamine, β-phenylethylamine, aniline, o-toluidine, m-toluidine and p-toluidine; aliphatic and aromatic secondary amines having 2 to 20 carbon atoms such as dimethylamine, methylethylamine, diethylamine, di-n-propylamine, ethyl-n-butylamine, methyl-sec-butylamine, dipentylamine, dicyclohexylamine, N-methylaniline and diphenylamine; polyamines having 2 to 20 carbon atoms and 2 to 3 primary or secondary amino groups such as ethylenediamine, di(2-aminoethyl)amine, hexamethylenediamine, 4,4'-diaminodiphenylmethane, melamine, tri(2-aminoethyl)amine, N,N'-dimethylethylenediamine and di(2-methylaminoethyl) amine; saturated cyclic secondary amines having 4 to 20 carbon atoms such as pyrrolidine, piperidine, morpholine and 1,2,3,4-tetrahydroquinoline; unsaturated cyclic secondary amines having 4 to 20 carbon atoms such as 3-pyrroline, pyrrole, indole, carbazole, imidazole, pyrazole and purine; cyclic polyamines having 4 to 20 carbon atoms and 2 to 3 secondary amino groups such as piperazine, pyrazine and 1,4,7-triazacyclononane; unsubstituted or N-monosubstituted acid amides having 2 to 20 carbon atoms acetamide, propionamide, N-methylpropionamide, N-methylbenzamide and N-ethylstearylamide; 5 to 7 member cyclic amides such as 2-pyrrolidone and ε-caprolactam; and dicarboxylic acid amides having 4 to 10 carbon atoms such as succinamide, maleimide and phthalimide.

The active hydrogen compound may include compounds having a plurality of active hydrogens. Polymerization is generally initiated from anion moieties generated after elimination of all the active hydrogen atoms as a proton.

Organic compounds having a partial structure of —OH as an active hydrogen compound may include alcohols having 1 to 20 carbon atoms such as methanol, ethanol, n-propanol, isopropanol, n-butyl alcohol, sec-butyl alcohol, tert-butyl alcohol, iso-pentyl alcohol, tert-pentyl alcohol, n-octyl alcohol, lauryl alcohol, cetyl alcohol, cyclopentanol, cyclohexanol, allyl alcohol, crotyl alcohol, methyl vinyl carbinol, benzyl alcohol, 1-phenylethyl alcohol, triphenyl carbinol and cinnamyl alcohol; polyhydric alcohols having 2 to 20 carbon atoms and 2 to 8 hydroxyl groups such as ethylene glycol, propylene glycol, diethylene glycol, dipropylene glycol, 1,3-propanediol, 1,3-butanediol, 1,4-butanediol, 1,6-hexanediol, 1,4-cyclohexanediol, trimethylolpropane, glycerin, diglycerin, pentaerythritol and dipentaerythritol; saccharides and their derivatives such as glucose, sorbitol, dextrose, fructose and sucrose; and poly (alkylene oxide)s having 2 to 8 terminal ends 1 to 8 hydroxyl groups at the terminal ends whose number-average molecular weight is 200 to 50,000, such as poly(ethylene oxide), poly(propylene oxide) and copolymers thereof.

Preferable organic compounds having a partial structure of —NH— are polyamines having 2 to 20 carbon atoms and 2 to 3 primary or secondary amino groups such as ethylenediamine, di(2-aminoethyl)amine, hexamethylenediamine, 4,4'-diaminodiphenylmethane, tri (2-aminoethyl)amine, N,N'-dimethylethylenediamine, N,N'-diethylethylenediamine and di(2-methylaminoethyl)amine; saturated cyclic secondary amines having 4 to 10 carbon atoms such as pyrrolidine, piperidine, morpholine and 1,2, 3,4-tetrahydroquinoline; and cyclic polyamines having 4 to 10 carbon atoms and 2 to 3 secondary amino groups such as piperazine, pyrazine and 1,4,7-triazacyclononane.

Organic compounds having a partial structure of —OH are more preferable as an active hydrogen compound, including polyhydric alcohols having 2 to 20 carbon atoms and 2 to 8 hydroxyl groups such as ethylene glycol, propylene glycol, 1,4-butanediol, trimethylolpropane, glycerin, pentaerythritol and dipentaerythritol; saccharides and their derivatives such as glucose, sorbitol, dextrose, fructose and sucrose; and poly(alkylene oxide)s having 2 to 6 terminal ends and 2 to 6 hydroxyl groups at the terminal ends whose number-average molecular weight is 200 to 10,000, such as poly(ethylene oxide), poly(propylene oxide) and copolymers thereof.

The amount of the phosphine sulfide represented by formula (1) is, but not limited to, generally $1\times10^{-15}$ to $5\times10^{-1}$ moles, preferably $1\times10^{-7}$ to $1\times10^{-1}$ moles to one mole of an alkylene oxide.

The amount of the active hydrogen compound is, but not limited to, generally 1 to $1\times10^5$ moles, preferably 5 to $1\times10^4$ moles, more preferably 10 to $1\times10^3$ moles to one mole of the phosphine sulfide.

Polymerization may be, but not limited to, generally conducted according to a procedure that an alkylene oxide is introduced in one portion, intermittently or continuously to a reaction vessel in which a phosphine sulfide represented by formula (1) or the phoshine sulfide and an active hydrogen compound are charged, together with a solvent when used.

A polymerization temperature may vary depending on a variety of factors such as the type of alkylene oxide used, the amount of a phosphine sulfide represented by formula (1) and the type and the amount of active hydrogen compound, but is generally below 150° C., preferably 10 to 130° C., more preferably 50 to 120° C. A reaction pressure may vary depending on a variety of factors such as the type of alkylene oxide used, type and the amount of active hydrogen compound and polymerization temperature, but is generally below 3.0 MPa (an absolute pressure expressed in mega pascal; hereinafter, the same definition is used), preferably 0.01 to 1.5 MPa, more preferably 0.1 to 1.0 MPa. A reaction duration may vary depending on a variety of factors such as types and the amounts of reactants, a polymerization temperature and polymerization pressure, but is generally within 70 hours, preferably 0.1 to 30 hours, more preferably 0.5 to 24 hours.

In a process for manufacturing a poly(alkylene oxide) of this invention, two or more alkylene oxides may be combined. Two or more alkylene oxides may be simultaneously used for polymerization to provide a relatively more random copolymer, depending on difference in reactivity between them. Two or more alkylene oxides may be sequentially used for polymerization to provide a block copolymer comprising blocks of two or more poly(alkylene oxide)s. For example, after the completion of the polymerization of the first alkylene oxide, the second alkylene oxide may be polymerized in situ to provide a block copolymer comprising two different blocks. After the completion of the polymerization of the second alkylene oxide, the first alkylene oxide may be again polymerized or the above procedure may be repeated to provide a alternating block copolymer. Three or more alkylene oxides may be combined as described above to provide a more complex block copolymer. Preferable copolymer is a block copolymer comprising blocks of poly(propylene oxide) and poly(ethylene oxide) prepared by sequentially polymerizing propylene oxide and ethylene oxide as an alkylene oxide.

In the polymerization reaction, a solvent may be, if necessary, used. Solvents which may be used include aliphatic hydrocarbons such as pentane, hexane, heptane and cyclohexane; aromatic hydrocarbons such as benzene and toluene; ethers such as diethyl ether, tetrahydrofuran, 1,3-dioxane and anisole; and aprotic polar solvents such as dimethylsulfoxide, N,N-dimethylformamide, hexamethylphosphoramide and N,N'-dimethyl imidazolidinone. Any other solvent may be used as long as it does not adversely affect the polymerization reaction in the process of this invention. The polymerization in the process for manufacturing a poly(alkylene oxide) of this invention may be, if necessary, conducted in an atmosphere of an inert gas such as nitrogen and argon.

The poly(alkylene oxide) prepared by the process of this invention may be sometimes used directly as a starting material for a polyurethane foam or elastomer or a surfactant after removing the solvent, when used. However it may be generally used after being treated with a mineral acid such as hydrochloric acid, phosphoric acid and sulfuric acid; an organic carboxylic acid such as formic acid, acetic acid and propionic acid; carbon dioxide; or an acid-type of ion-exchange resin.

It may be purified as usual by, for example, washing with water, an organic solvent or a mixture thereof.

The fourth aspect of this invention will be described. The fourth aspect of this invention is a process for manufacturing a 1,2-dioxyethane derivative having a partial structure represented by formula (3), (4), (5) or (6), comprising reacting an epoxy compound with a carboxylate, carboxylic anhydride, carbonate or phenol compound, respectively, in the presence of a phosphine sulfide represented by formula (1).

An epoxy compound is an organic compound comprising a three-membered epoxy group, including aliphatic, alicyclic and aromatic epoxy compounds consisting of carbon and hydrogen atoms and an oxygen atom of the epoxy group; aliphatic, alicyclic and aromatic epoxy compounds containing a halogen atom; aliphatic, alicyclic and aromatic epoxy compounds having a keto group; aliphatic, alicyclic and aromatic epoxy compounds having an ether bond; aliphatic, alicyclic and aromatic epoxy compounds having an ester bond; aliphatic, alicyclic and aromatic epoxy compounds having a tertiary amino group; and aliphatic, alicyclic and aromatic epoxy compounds having a cyano group.

Specific epoxy compounds include aliphatic epoxy compounds consisting of carbon and hydrogen atoms and an oxygen atom of the epoxy group such as ethylene oxide, propylene oxide, 1,2-epoxybutane, 2,3-epoxybutane, 1,2-epoxyhexane, 1,2-epoxyoctane, 1,2-epoxydecane, 1,2-epoxydodecane, 1,2-epoxytetradecane, 1,2-epoxyhexadecane, 1,2-epoxyoctadecane, 7,8-epoxy-2-methyloctadecane, 2-vinyloxirane, 2-methyl-2- vinyloxirane, 1,2-epoxy-5-hexene, 1,2-epoxy-7-octene, 1-phenyl-2,3-epoxypropane, 1-(1-naphthyl)-2,3-epoxypropane, 1-cyclohexyl-3,4-epoxybutane, 1,3-butadiene dioxide and 1,2,7,8-diepoxyoctane; alicyclic epoxy compounds consisting of carbon and hydrogen atoms and an oxygen atom of the epoxy group such as cyclopentene oxide, 3-methyl-1,2-cyclopentene oxide, cyclohexene oxide, cyclooctene oxide, α-pinene oxide, 2,3-epoxynorbornane, limonene oxide, cyclododecane epoxide and 2,3,5,6-diepoxynorbornane; aromatic epoxy compounds consisting of carbon and hydrogen atoms and an oxygen atom of the epoxy group such as styrene oxide, 3-methylstyrene oxide, 1,2-epoxybutylbenzene, 1,2-epoxyoctylbenzene, stilbene oxide, 3-vinylstyrene oxide, 1-(1-methyl-1,2-epoxyethyl)-3-(1-methylvinyl)benzene, 1,4-bis(1,2-epoxypropyl)benzene, 1,3-bis(1,2-epoxy-1-methylethyl)benzene and 1,4-bis(1,2-epoxy-1-methylethyl)benzene; halogenated aliphatic epoxy compounds such as epifluorohydrin, epichlorohydrin, epibromohydrin, hexafluoropropylene oxide, 1,2-epoxy-4-fluorobutane, 1-(2, 3-epoxypropyl)-4-fluorobenzene, 1-(3,4-epoxybutyl)-2-fluorobenzene, 1-(2,3-epoxypropyl)-4-chlorobenzene and 1-(3,4-epoxybutyl)-3-chlorobenzene; halogenated alicyclic epoxy compounds such as 4-fluoro-1,2-cyclohexene oxide and 6-chloro-2,3-epoxybicyclo[2.2.1]heptane; halogenated aromatic epoxy compounds such as 4-fluorostyrene oxide and 1-(1,2-epoxypropyl)-3-trifluorobenzene; aliphatic epoxy compounds having a keto group such as 3-acetyl-1, 2-epoxypropane, 4-benzoyl- 1,2-epoxybutane, 4-(4-benzoyl)phenyl-1,2-epoxybutane and 4,4'-bis(3,4-epoxybutyl)benzophenone; alicyclic epoxy compounds having a keto group such as 3,4-epoxy-1-cyclohexanone and 2,3-epoxy-5-oxobicyclo[2.2.1]heptane; aromatic epoxy compounds having a keto group such as 3-acetylstyrene oxide and 4-(1,2-epoxypropyl)benzophenone; aliphatic epoxy compounds having an ether bond such as glycidyl methyl ether, butyl glycidyl ether, 2-ethylhexyl glycidyl ether, allyl glycidyl ether, ethyl 3,4-epoxybutyl ether, glycidyl phenyl ether, glycidyl 4-tert-butylphenyl ether, glycidyl 4-chlorophenyl ether, glycidyl 4-methoxyphenyl ether, glycidyl 2-phenylphenyl ether, glycidyl 1-naphthyl ether, glycidyl 4-indolyl ether, glycidyl N-methyl-α-quinolon-4-yl ether, ethyleneglycol diglycidyl ether, 1,4-butanediol diglycidyl ether, 1,2-diglycidyloxybenzene, 2,2-bis(4-glycidyloxyphenyl)propane, tris(4-glycidyloxyphenyl)methane, poly(oxypropylene)triol triglycidyl ether and a glycidyl ether of phenol novolac; alicyclic epoxy compounds having an ether bond such as 1,2-epoxy-4-methoxycyclohexane and 2,3-epoxy-5,6-dimethoxybicyclo[2.2.1]heptane; aromatic epoxy compounds having an ether bond such as 4-methoxystyrene oxide and 1-(1,2-epoxybutyl)-2-phenoxybenzene; aliphatic epoxy compounds having an ester bond such as glycidyl formate, glycidyl acetate, 2,3-epoxybutyl acetate, glycidyl butyrate, glycidyl benzoate, diglycidyl terephthalate, poly(glycidyl acrylate), poly(glycidyl methacrylate), a copolymer of glycidyl acrylate with another monomer and a copolymer of glycidyl methacrylate with another monomer; alicyclic epoxy compounds having an ester bond such as 1,2-epoxy-4-methoxycarbonylcyclohexane and 2,3-epoxy-5-butoxycarbonylbicyclo[2.2.1]heptane; aromatic epoxy compounds having an ester bond such as ethyl 4-(1,2-epoxyethyl)benzoate, methyl 3-(1,2-epoxybutyl)benzoate and methyl 3-(1,2-epoxybutyl)-5-phenylbenzoate; aliphatic epoxy compounds having a tertiary amino group such as N,N-glycidylmethylacetamide, N,N-ethylglycidylpropionamide, N,N-glycidylmethylbenzamide, N-(4,5-epoxypentyl)-N-methylbenzamide, N,N-diglycidylaniline, bis(4-diglycidylaminophenyl)methane and poly(N,N-glycidylmethylacrylamide); alicyclic epoxy compounds having a tertiary amino group such as 1,2-epoxy-3-(diphenylcarbamoyl)cyclohexane and 2,3-epoxy-6-(dimethylcarbamoyl)bicyclo[2.2.1]heptane; aromatic epoxy compounds having a tertiary amino group such as 2-(dimethylcarbamoyl)styrene oxide and 4-(1,2-epoxybutyl)-4'-(dimethylcarbamoyl)biphenyl; aliphatic epoxy compounds having a cyano group such as 4-cyano-1,2-epoxybutane and 1-(3-cyanophenyl)-2,3-epoxybutane; and alicyclic epoxy compounds having a cyano group such as 2-cyanostyrene oxide and 6-cyano-1-(1,2-epoxy-2-phenylethyl)naphthalene.

These compounds may have any other bond, substituent or hetero atom as long as it does not adversely affect the process of this invention.

Preferable epoxy compounds are (a) the above aliphatic and aromatic epoxy compounds consisting of carbon and hydrogen atoms and an oxygen atom of the epoxy group; (b) the above aliphatic and aromatic epoxy compounds having an ether bond; and (c) the above aliphatic and aromatic epoxy compounds having an ester bond.

More preferable epoxy compounds are aliphatic epoxy compounds consisting of carbon and hydrogen atoms and an oxygen atom of the epoxy group such as ethylene oxide, propylene oxide, 1,2-epoxybutane, 2,3-epoxybutane, 1,2-epoxyhexane, 1,2-epoxyoctane, 1,2-epoxydecane, 1,2-epoxydodecane, 1,2-epoxytetradecane, 1,2-epoxyhexadecane, 1,2-epoxyoctadecane, 7,8-epoxy-2-methyloctadecane, 2-vinyloxirane, 2-methyl-2-vinyloxirane, 1,2-epoxy-5-hexene, 1,2-epoxy-7-octene, 1-phenyl-2,3-epoxypropane, 1-(1-naphthyl)-2,3-epoxypropane, 1-cyclohexyl-3,4-epoxybutane, 1,3-butadiene dioxide and 1,2,7,8-diepoxyoctane; aliphatic epoxy compounds having an ether bond such as glycidyl methyl ether, butyl glycidyl ether, 2-ethylhexyl glycidyl ether, allyl glycidyl ether, ethyl 3,4-epoxybutyl ether, glycidyl phenyl ether, glycidyl 4-tert-butylphenyl ether, glycidyl 4-chlorophenyl ether, glycidyl 4-methoxyphenyl ether, glycidyl 2-phenylphenyl ether, glycidyl 1-naphthyl ether, glycidyl 4-indolyl ether, glycidyl N-methyl-α-quinolon-4-yl ether, ethyleneglycol diglycidyl ether, 1,4-butanediol diglycidyl ether, 1,2-diglycidyloxybenzene, 2,2-bis(4-glycidyloxyphenyl)propane, tris(4-glycidyloxyphenyl)methane, poly(oxypropylene)triol triglycidyl ether and a glycidyl ether of phenol novolac; and aliphatic epoxy compounds having an ester bond such as glycidyl formate, glycidyl acetate, 2,3-epoxybutyl acetate, glycidyl butyrate, glycidyl benzoate, diglycidyl terephthalate, poly(glycidyl acrylate), poly(glycidyl methacrylate), a copolymer of glycidyl acrylate with another monomer and a copolymer of glycidyl methacrylate with another monomer.

In the process of this invention, a 1,2-dioxyethane derivative prepared by reacting an epoxy compound with a carboxylate in the presence of a phosphine sulfide represented by formula (1) is a compound in which the cleaved epoxy group in the epoxy compound is inserted between the acyl group and the alkoxy or aryloxy group in the ester bond in the carboxylate, having a partial structure represented by formula (3) where a carbon atom C— or —C attached to the carbonyl group or the oxygen atom belongs to an aliphatic, alicyclic or aromatic hydrocarbon.

Carboxylates which may be used include aliphatic, alicyclic and aromatic carboxylates consisting of carbon and hydrogen atoms and oxygen atoms of the ester bond; halogenated aliphatic, alicyclic and aromatic carboxylates;

aliphatic, alicyclic and aromatic carboxylates having an ether bond; aliphatic, alicyclic and aromatic carboxylates having a cyano group; and aliphatic, alicyclic and aromatic carboxylates having a keto group.

Specific carboxylates include aliphatic carboxylates consisting of carbon and hydrogen atoms and oxygen atoms of the ester bond such as methyl formate, ethyl formate, methyl acetate, ethyl acetate, n-butyl acetate, iso-propyl propionate, methyl butyrate, n-octyl butyrate, n-decyl isobutyrate, vinyl acetate, methyl laurate, allyl stearate, cyclohexyl oleate, phenyl phenylacetate, 1,2-diacetoxyethane, triacetin, 1,2-diacetoxybenzene, 2,6-diacetoxynaphthalene, 4,4'-diacetoxybiphenyl, 2,2-bis(4-acetoxyphenyl)propane, phenol novolac acetate, poly(butadiene)diol acetate, poly (isobutene)diol acetate, poly(vinyl acetate), poly(lactic acid), poly(caprolactone), dimethyl oxalate, diethyl oxalate, dimethyl malonate, dimethyl succinate, diphenyl succinate, dimethyl adipate, di-n-octyl adipate, di(4-methylphenyl) 1,10-decanedicarboxylate, tetraphenyl 1,2,3,4-butanetetracarboxylate, dimethyl poly(butadiene) dicarboxylate, poly(methyl acrylate), poly(methyl methacrylate), a copolymer of glycidyl acrylate with another monomer, a copolymer of glycidyl methacrylate with another monomer, diethyl maleate, dimethyl fumarate, di-t-butyl fumarate and dimethyl itaconate; alicyclic carboxylates consisting of carbon and hydrogen atoms and oxygen atoms of the ester bond such as 1-naphthyl cyclohexanecarboxylate, ethyl 2-norbornanecarboxylate, phenyl 2-norbornenecarboxylate, diethyl 1,2-cyclobutanedicarboxylate, diphenyl 1,4-cyclohexanedicarboxylate, tri-n-octyl 1,2,4-cyclohexanetricarboxylate, tetra-n-octyl 1,2,4,5-cyclohexanetetracarboxylate, dimethyl 2,5-norbornanedicarboxylate, trimethyl 5-nonbornane-2,5,6-tricarboxylate and ethyl 1,3-adamantanecarboxylate; aromatic carboxylates consisting of carbon and hydrogen atoms and oxygen atoms of the ester bond such as methyl benzoate, octadecyl benzoate, 2-methylbutyl p-methylbenzoate, methyl 1-naphthalenecarboxylate, n-hexyl 2-naphthalenecarboxylate, 4,4'-dibenzoyloxybiphenyl, 2,2-bis(4-benzoyloxyphenyl) propane, phenol novolac benzoate, dimethyl phthalate, dimethyl isophthalate, diethyl terephthalate, tributyl trimellitate, tetraoctyl pyromellitate and polyethylene terephthalate; halogenated aliphatic carboxylates such as 4-fluorophenyl acetate, methyl 4-chlorobutyrate, phenyl 5-fluoro-2-hexanoate, ethyl pentafluorophenylacetate, 4-fluorophenyl 4-chlorophenylacetate, 1,2-diacetoxy-3-chlorobenzene, 2,6-diacetoxy-3-bromonaphthalene, 4,4'-diacetoxy-3,3',5,5'-tetrabromobiphenyl, 2,2-bis(4-acetoxy-3,5-dibromophenyl) propane and 2,2-bis(4-acetoxyphenyl)-1,1,1,3,3,3-hexafluoropropane; halogenated alicyclic carboxylates such as isopropyl 3-bromocyclohexanecarboxylate, pentafluorophenyl 3-fluorocyclohexanecarboxylate, n-octyl 5-chloro-2-bicyclo[2.2.1]heptanecarboxylate, di(4-iodophenyl) 1,4-cyclohexanedicarboxylate and tri(3-fluoro-n-octyl) 1,2,4-cyclohexanetricarboxylate; halogenated aromatic carboxylates such as pentafluorophenyl acetate, 4-chlorophenyl 4-bromobenzoate, cyclohexyl 4-chlorobenzoate, methyl pentafluorobenzoate, t-butyl 6-iodo-1-naphthalenecarboxylate, 1,2-dibenzoyloxy-3-chlorobenzene, 2,6-dibenzoyloxy-3-bromonaphthalene, 4,4'-dibenzoyloxy-3,3',5,5'-tetrabromobiphenyl, 2,2-bis(4-benzoyloxy-3,5-dibromophenyl)propane and 2,2-bis(4-benzoyloxyphenyl)-1,1,1,3,3,3-hexafluoropropane; aliphatic carboxylates having an ether bond such as methyl methoxyacetate, 4-methoxyphenyl acetate, n-octyl 2-methoxypropionate, 2-methoxyethyl 2-methoxypropionate, ethyl 4-(4-methylphenoxy)butyrate, n-butyl 3-phenoxyphenylacetate, di(2-acetoxy)ethyl ether, dipropyleneglycol acetate, pentaacetylglucose, poly (oxyethylene)diol acetate, poly(oxypropylene)triol acetate and naphthyl 2,2'-ethylenedioxy-diacetate; alicyclic carboxylates having an ether bond such as 2-phenoxyethyl 4-methoxycyclohexanecarboxylate, n-octyl 3-benzyloxycyclohexanecarboxylate and t-butyl 5,6-dimethoxy-2-bicyclo[2.2.1]heptanecarboxylate; aromatic carboxylates having an ether bond such as cyclohexyl 3-phenoxybenzoate, 2-methoxyethyl benzoate, 3-butoxypropyl 4-phenoxybenzoate, di(2-benzoyloxy)ethyl ether, dipropyleneglycol benzoate, n-hexadecyl 5-methoxyisophthalate and phenyl 4,4'-ethylenedioxybenzoate; aliphatic carboxylates having a cyano group such as methyl cyanoacetate, 2-cyanoethyl acetate, 4-cyanophenyl 2-(3-cyanophenyl)propionate, 4-cyanophenyl acetate and 2-cyanocyclohexyl propionate; alicyclic carboxylates having a cyano group such as 4-cyanobutyl cyclohexanecarboxylate, 2-cyanocyclohexyl 3-cyanocyclohexanecarboxylate and dimethyl 5-cyano-2-norbornanecarboxylate; aromatic carboxylates having a cyano group such as 3-cyanopropyl benzoate, 4-cyanophenyl 2-cyanobenzoate, phenyl 4-cyanobenzoate and ethyl 6-cyano-2-naphthalenecarboxylate; aliphatic carboxylates having a keto group such as methyl glycolate, 3-oxobutyl acetate, 4-oxocyclohexyl acetoacetate, phenyl pyruvate and ethyl acetoacetate; alicyclic carboxylates having a keto group such as methyl 3-oxo-1-cyclopentanecarboxylate, 3-oxobutyl 4-oxo-1-cyclohexanecarboxylate, 4-oxocyclohexyl cyclohexanecarboxylate and n-butyl 3-acetyl-1-cyclohexanecarboxylate; and aromatic carboxylates having a keto group such as 1-naphthyl 4-acetylbenzoate, 2-benzoylethyl benzoate, 2-oxobutyl 4-benzoylbenzoate and naphthyl 5-acetylnaphthalene-1-carboxylate.

These carboxylates are, as a whole compound, aliphatic, alicyclic and aromatic carboxylates consisting of carbon and hydrogen atoms and oxygen atoms of the ester bond; halogenated aliphatic, alicyclic and aromatic carboxylates; aliphatic, alicyclic and aromatic carboxylates having an ether bond; aliphatic, alicyclic and aromatic carboxylates having a cyano group; and aliphatic, alicyclic and aromatic carboxylates having a keto group. These substituents or functional groups may be contained either in a carboxylic moiety or in a hydroxyl moiety or in both moieties in an ester group. A hydroxyl moiety consisting of an ester group may be aliphatic, alicyclic or aromatic.

Carboxylates for the process of this invention may have any other substituent, functional group or hetero atom as long as it does not adversely affect the process of this invention.

Preferable carboxylates are (a) the above aliphatic and aromatic carboxylates consisting of carbon and hydrogen atoms and oxygen atoms of the ester bond; and (b) the above aliphatic and aromatic carboxylates having an ether bond.

More preferable carboxylates are aliphatic carboxylates consisting of carbon and hydrogen atoms and oxygen atoms of the ester bond such as methyl formate, ethyl formate, methyl acetate, ethyl acetate, n-butyl acetate, iso-propyl propionate, methyl butyrate, n-octyl butyrate, n-decyl isobutyrate, vinyl acetate, methyl laurate, allyl stearate, cyclohexyl oleate, phenyl phenylacetate, 1,2-diacetoxyethane, triacetin, 1,2-diacetoxybenzene, 2,6-diacetoxynaphthalene, 4,4'-diacetoxybiphenyl, 2,2-bis(4-acetoxyphenyl)propane, phenol novolac acetate, poly (butadiene)diol acetate, poly(isobutene)diol acetate, poly (vinyl acetate), poly(lactic acid), poly(caprolactone), dimethyl oxalate, diethyl oxalate, dimethyl malonate, dimethyl succinate, diphenyl succinate, dimethyl adipate, di-n-octyl adipate, di(4-methylphenyl) 1,10-decanedicarboxylate, tetraphenyl 1,2,3,4-butanetetracarboxylate, dimethyl poly(butadiene) dicarboxylate, poly(methyl acrylate), poly(methyl methacrylate), a copolymer of glycidyl acrylate with another monomer, a copolymer of glycidyl methacrylate with another monomer, diethyl maleate, dimethyl fumarate, di-t-butyl fumarate and dimethyl itaconate; and aliphatic carboxylates having an ether bond such as methyl methoxyacetate, 4-methoxyphenyl acetate, n-octyl 2-methoxypropionate, 2-methoxyethyl 2-methoxypropionate, ethyl 4-(4-methylphenoxy)butyrate, n-butyl 3-phenoxyphenylacetate, di(2-acetoxy)ethyl ether, dipropyleneglycol acetate, pentaacetylglucose, poly(oxyethylene)diol acetate, poly(oxypropylene)triol acetate and naphthyl 2,2'-ethylenedioxy-diacetate.

In the process of this invention, a 1,2-dioxyethane derivative prepared by reacting an epoxy compound with a carboxylic anhydride in the presence of a phosphine sulfide represented by formula (1) is a compound in which the cleaved epoxy group in the epoxy compound is inserted between the acyl group and the acyloxy group in the carboxylic anhydride group in the carboxylic anhydride, having a partial structure represented by formula (4) where a carbon atom C— or —C attached to the carbonyl group belongs to an aliphatic, alicyclic or aromatic hydrocarbon.

Carboxylic anhydrides which may be used include aliphatic, alicyclic and aromatic carboxylic anhydrides consisting of carbon and hydrogen atoms and oxygen atoms of the carboxylic anhydride group; aliphatic, alicyclic and aromatic carboxylic anhydrides having an ether bond; and aliphatic, alicyclic and aromatic carboxylic anhydrides having a keto group.

Specific carboxylic anhydrides include aliphatic carboxylic anhydrides consisting of carbon and hydrogen atoms and oxygen atoms of the carboxylic anhydride group such as acetic anhydride, propionic anhydride, butyric anhydride, isobutyric anhydride, valeric anhydride, isovaleric anhydride, tetramethylacetic anhydride, hexanoic anhydride, heptanoic anhydride, decanoic anhydride, lauric anhydride, palmitic anhydride, stearic anhydride, docosanoic anhydride, oleic anhydride, linolic anhydride, phenylacetic anhydride, a mixed acid anhydride from suberic acid and formic acid, a mixed acid anhydride from suberic acid and acetic acid, 1,6-di(formyloxycarbonyl) hexane, 1,6-di(acetoxycarbonyl)hexane, 1,8-di(acetoxycarbonyl)octane and a mixed acid anhydride from poly(butadiene)dicarboxylic acid and acetic acid; alicyclic carboxylic anhydrides consisting of carbon and hydrogen atoms and oxygen atoms of the carboxylic anhydride group such as cyclobutanecarboxylic anhydride, cyclopentanecarboxylic anhydride, cyclohexanecarboxylic anhydride, cycloheptanecarboxylic anhydride, 1-adamantanecarboxylic anhydride, norbornane-2-carboxylic anhydride, norbornene-2-carboxylic anhydride, 1,4-di(formyloxycarbonyl) cyclohexane, 1,3-di(acetoxycarbonyl)adamantane and 1,3,5-tri(acetoxycarbonyl)cyclohexane; aromatic carboxylic anhydrides consisting of carbon and hydrogen atoms and oxygen atoms of the carboxylic anhydride group such as benzoic anhydride, acetoxycarbonylbenzene, 4-butylbenzoic anhydride, 1-naphthalenecarboxylic anhydride, 2-naphthalenecarboxylic anhydride, 1-methylnaphthalene-2-carboxylic anhydride, biphenylenecarboxylic anhydride, 4-fluorenecarboxylic anhydride, 9-anthracenecarboxylic anhydride, trimellitic anhydride, 1,3-di(formyloxycarbonyl)benzene, 1,4-di(acetoxycarbonyl)benzene, 1,3,4-tri(acetoxycarbonyl) benzene, 1,3,5-tri(acetoxycarbonyl)benzene, 2,6-di(acetoxycarbonyl)naphthalene and 1,3,6-tri(acetoxycarbonyl)naphthalene; aliphatic carboxylic anhydrides having an ether bond such as 2-methoxyacetic anhydride, 3-phenoxypropionic anhydride, glutaric anhydride, 8-butoxyoctanoic anhydride, di(2-acetoxycarbonyl)ethyl ether, di(2-acetoxycarbonylethoxy) ethane and a mixed acid anhydride from poly(oxypropylene) dicarboxylic acid and acetic acid; alicyclic carboxylic anhydrides having an ether bond such as 4-methoxycyclohexanecarboxylic anhydride, 3-phenoxycycloheptanecarboxylic anhydride, 5,6-dimethoxynorbornane-2-carboxylic anhydride, 7-butoxynorbornene-2-carboxylic anhydride and 7-oxobicyclo[2.2.1]hexane-2-carboxylic anhydride; aromatic carboxylic anhydrides having an ether bond such as 3-methoxybenzoic anhydride, 3,4-dimethoxybenzoic anhydride, 2-phenoxybenzoic anhydride, 3-phenoxybenzoic anhydride, 1,4-di(acetoxycarbonyl)-2-butoxybenzene, 1,3,4-tri(acetoxycarbonyl)-5-phenoxybenzene, 1,3,5-tri(acetoxycarbonyl)-4-methoxybenzene and 2,6-di(acetoxycarbonyl)-1-isopropoxynaphthalene; aliphatic carboxylic anhydrides having a keto group such as pyruvic anhydride, 2-ketobutyric anhydride, 7-oxooctanoic anhydride and a mixed acid anhydride from 4-ketopimelic acid and acetic acid; and aromatic carboxylic anhydrides having a keto group such as 4-acetylbenzoic anhydride, 4-benzoylbenzoic anhydride, 9-fluorenone-1-carboxylic anhydride, 9-fluorenone-2-carboxylic anhydride, 9-fluorenone-4-carboxylic anhydride and anthraquinone-2-carboxylic anhydride. Carboxylic anhydrides for the process of this invention may have any other substituent or hetero atom as long as it does not adversely affect the process of this invention.

Preferable carboxylic anhydrides are the above aliphatic and aromatic carboxylic anhydrides consisting of carbon and hydrogen atoms and oxygen atoms of the carboxylic anhydride group.

More preferable carboxylic anhydrides are aromatic carboxylic anhydrides consisting of carbon and hydrogen atoms and oxygen atoms of the carboxylic anhydride group such as benzoic anhydride, acetoxycarbonylbenzene, 4-butylbenzoic anhydride, 1-naphthalenecarboxylic anhydride, 2-naphthalenecarboxylic anhydride, 1-methylnaphthalene-2-carboxylic anhydride, biphenylenecarboxylic anhydride, 4-fluorenecarboxylic anhydride, 9-anthracenecarboxylic anhydride, trimellitic anhydride, 1,3-di(formyloxycarbonyl)benzene, 1,4-di(acetoxycarbonyl)benzene, 1,3,4-tri(acetoxycarbonyl) benzene, 1,3,5-tri(acetoxycarbonyl)benzene, 2,6-di(acetoxycarbonyl)naphthalene and 1,3,6-tri(acetoxycarbonyl)naphthalene.

In the process of this invention, a 1,2-dioxyethane derivative prepared by reacting an epoxy compound with a carbonate in the presence of a phosphine sulfide represented by formula (1) is a compound in which the cleaved epoxy group in the epoxy compound is inserted between the alkoxy- or aryloxycarbonyl group and the alkoxy or aryloxy group in the carbonate group in the carbonate, having a partial structure represented by formula (5) where a carbon atom C— or —C attached to the oxygen atom belongs to an aliphatic, alicyclic or aromatic hydrocarbon.

Carbonates which may be used include aliphatic, alicyclic and aromatic carbonates consisting of carbon and hydrogen atoms and oxygen atoms of the carbonate group; halogenated aliphatic, alicyclic and aromatic carbonates; and aliphatic, alicyclic and aromatic carbonates having an ether bond.

Specific carbonates include aliphatic carbonates consisting of carbon and hydrogen atoms and oxygen atoms of the carbonate group such as dimethyl carbonate, n-octyl methyl carbonate, di-n-butyl carbonate, 1,4-di(methoxycarbonyloxy)butane, 1,8-di(ethoxycarbonyloxy)octane, poly(ethylene carbonate) and poly(propylene carbonate); alicyclic carbonates consisting of carbon and hydrogen atoms and oxygen atoms of the carbonate group such as cyclohexyl isopropyl carbonate, dicyclohexyl carbonate, 1,4-di(methoxycarbonyloxy)cyclohexane and 1,3,5-tri(methoxycarbonyloxy)cyclohexane; aromatic carbonates consisting of carbon and hydrogen atoms and oxygen atoms of the carbonate group such as methyl phenyl carbonate, diphenyl carbonate, 1,4-di(methoxycarbonyloxy)benzene, 2,2-bis(4-methoxycarbonyloxyphenyl)propane, 2,2-bis(4-benzoyloxycarbonyloxyphenyl)propane and phenol novolac methyl carbonate; halogenated aliphatic carboxylates such as 8-fluorooctyl methyl carbonate, di(3-bromobutyl) carbonate, 1,4-di(methoxycarbonyloxy)-2-chlorobutane and 1,8-di(ethoxycarbonyloxy)-4,5,6-trifluorooctane; halogenated aromatic carboxylates such as methyl 4-iodophenyl carbonate, di(2-chlorophenyl) carbonate, 1,4-di(methoxycarbonyloxy)-2,3,5,6-tetrabromobenzene, 2,2-bis(4-methoxycarbonyloxy-3,5-dibromophenyl)propane and 2,2-bis(4-benzoyloxycarbonyloxy-3,5-dichlorophenyl)propane; aliphatic carbonates having an ether bond such as di-2-(methoxycarbonyloxy)ethyl ether, poly(oxyethylene)diol methyl carbonate and poly(oxypropylene)triol methyl carbonate; and aromatic carbonates having an ether bond such as di-4-(methoxycarbonyloxy)phenyl ether and di-2-(methoxycarbonyloxy)-1-naphthyl ether. Carbonates for the process of this invention may have any other substituent or hetero atom as long as it does not adversely affect the process of this invention.

Preferable carbonates are (a) the above aliphatic and aromatic carbonates consisting of carbon and hydrogen atoms and oxygen atoms of the carbonate group; and (b) the above aliphatic and aromatic carbonates having an ether bond.

More preferable carbonates are aliphatic carbonates consisting of carbon and hydrogen atoms and oxygen atoms of the carbonate group such as dimethyl carbonate, n-octyl methyl carbonate, di-n-butyl carbonate, 1,4-di(methoxycarbonyloxy)butane, 1,8-di(ethoxycarbonyloxy)octane, poly(ethylene carbonate) and poly(propylene carbonate); aromatic carbonates consisting of carbon and hydrogen atoms and oxygen atoms of the carbonate group such as methyl phenyl carbonate, diphenyl carbonate, 1,4-di(methoxycarbonyloxy)benzene, 2,2-bis(4-methoxycarbonyloxyphenyl)propane, 2,2-bis(4-benzoyloxycarbonyloxyphenyl)propane and phenol novolac methyl carbonate; and aliphatic carbonates having an ether bond such as di-2-(methoxycarbonyloxy)ethyl ether, poly(oxyethylene)diol methyl carbonate and poly(oxypropylene) triol methyl carbonate.

In the process of this invention, a 1,2-dioxyethane derivative prepared by reacting an epoxy compound with a phenol compound in the presence of a phosphine sulfide represented by formula (1) is a compound in which the cleaved epoxy group in the epoxy compound is inserted between the phenoxy group and the hydrogen atom in the phenol compound, having a partial structure represented by formula (6) where a carbon atom —C attached to the oxygen atom belongs to an aromatic hydrocarbon.

Phenol compounds which may be used include phenol compounds consisting of carbon and hydrogen atoms and an oxygen atom of the phenolic hydroxyl group such as phenol, cresol, 3-isopropylphenol, 4-butylphenol, 2-cyclopentylphenol, 2,3-dimethylphenol, 2,3,6-trimethylphenol, 2,6-diisopropylphenol, 3,5-di-tert-butylphenol, 2,6-di-tert-butyl-4-methylphenol, 5-indanol, 5,6,7,8-tetrahydro-1-naphthol, naphthol, nonylphenol, 4-hydroxystyrene, 4-hydroxy-α-methylstyrene, 1,1'-bi-2-naphthol, catechol, resorcinol, hydroquinone, 2-methylresorcinol, 4-hexylresorcinol, 2,6-dihydroxynaphthalene, bis(4-hydroxyphenyl)methane, 2,2-bis(4-hydroxyphenyl)propane, 2,2-bis(4-hydroxy-3-methylphenyl)propane, 2,2'-biphenol, 4,4'-biphenol, phenylhydroquinone, 1,3,5-trihydroxybenzene, 2,4-bis(4-hydroxyphenyl)-4-methyl-1-pentene, 2,4,6-tris(4-hydroxyphenyl)-2,6-dimethyl-3-hexene, 5-hydroxy-3-(4-hydroxyphenyl)-1,1,3-trimethyl-2,3-dihydroindene, 5-hydroxy-3-(4-hydroxyphenyl)-2,6-dimethyl-3-hexene, tri(4-hydroxyphenyl)methane, phenol novolac, poly(4-hydroxystyrene) and poly(4-hydroxy-α-methylstyrene); halogenated phenol compounds such as 3-fluorophenol, 2-trifluoromethylphenol, 4-chlorophenol, 2-bromophenol, 2,6-difluorophenol, 4-fluoro-2-methylphenol, 2,3,4-trichlorophenol, 2,2-bis(4-hydroxy-3,5-dichlorophenyl)propane, 2,2-bis(4-hydroxyphenyl)-1,1,1,2,2,2-hexafluoropropane, octafluoro-4,4'-biphenol and 6,6'-dibromo-1,1'-bi-2-naphthol; phenol compounds having an ether bond such as 2-ethoxyphenol, 4-(phenoxymethyl)phenol, 3,4,5-trimethoxyphenol, 7-methoxy-2-naphthol, 4-benzyloxy-3-methoxyphenol and 3,3'-(ethylenedioxy)diphenol; phenol compounds having a keto group such as 3-hydroxyacetophenone, 2-(2-oxopropyl)phenol, 4-hydroxybenzophenone, 1-hydroxy-2-acetonaphthone, 4,4'-dihydroxybenzophenone, 2,6-dihydroxyacetophenone and phloretin; phenol compounds having an ester bond such as 4-acetoxymethylphenol, methyl salicylate, 4-hydroxybenzyl acrylate, ethyl 4-hydroxy-3-methoxycinnamate, 2-methoxycarbonyl-6-methyl-3-naphthol, 1,2-bis(4-hydroxybenzoyloxy)ethane and ethyl 3,4,5-trihydroxybenzoate; and phenol compounds having an amide bond such as 4-acetaminophenol, 3-(N,N-dimethylcarbamoyl)phenol, 4-(N,N-dimethylcarbamoyl)-3-methylphenol, N-(3-hydroxy-5-methyl)phenylacrylamide, N-(5-hydroxy-8-methyl-2-naphthyl)methacrylamide, N-(4-hydroxybenzyl)benzamide and N,N'-bis(4-hydroxyphenyl)-5-methyl-1,3-benzenedicarboxamide. These compounds may have any other substituent or hetero atom as long as it does not adversely affect the process of this invention.

Preferable phenol compounds are (a) phenol compounds consisting of carbon and hydrogen atoms and an oxygen atom of the phenolic hydroxyl group such as phenol, cresol, 3-isopropylphenol, 4-butylphenol, 2-cyclopentylphenol, 2,3-dimethylphenol, 2,3,6-trimethylphenol, 2,6-diisopropylphenol, 3,5-di-tert-butylphenol, 2,6-di-tert-butyl-4-methylphenol, 5-indanol, 5,6,7,8-tetrahydro-1-naphthol, naphthol, nonylphenol, 4-hydroxystyrene, 4-hydroxy-α-methylstyrene, 1,1'-bi-2-naphthol, catechol, resorcinol, hydroquinone, 2-methylresorcinol, 4-hexylresorcinol, 2,6-dihydroxynaphthalene, bis(4-hydroxyphenyl)methane, 2,2-bis(4-hydroxyphenyl)propane, 2,2-bis(4-hydroxy-3-methylphenyl)propane, 2,2'-biphenol, 4,4'-biphenol, phenylhydroquinone, 1,3,5-trihydroxybenzene, 2,4-bis(4-hydroxyphenyl)-4-methyl-1-pentene, 2,4,6-tris(4-hydroxyphenyl)-2,6-dimethyl-3- hexene, 5-hydroxy-3-(4-hydroxyphenyl)-1,1,3-trimethyl-2,3-dihydroindene, 5-hydroxy-3-(4-hydroxyphenyl)-2,6-dimethyl-3-hexene, tri(4-hydroxyphenyl)methane, phenol novolac, poly(4-hydroxystyrene) and poly(4-hydroxy-α-methylstyrene); (b) halogenated phenol compounds such as 3-fluorophenol, 2-trifluoromethylphenol, 4-chlorophenol, 2-bromophenol, 2,6-difluorophenol, 4-fluoro-2-methylphenol, 2,3,4-trichlorophenol, 2,2-bis(4-hydroxy-3,5-dichlorophenyl)propane, 2,2-bis(4-hydroxyphenyl)-1,1,1,2,2,2-hexafluoropropane, octafluoro-4,4'-biphenol and 6,6'-dibromo-1,1'-bi-2-naphthol; and (c) phenol compounds having an ether bond such as 2-ethoxyphenol, 4-(phenoxymethyl)phenol, 3,4,5-trimethoxyphenol, 7-methoxy-2-naphthol, 4-benzyloxy-3-methoxyphenol and 3,3'-(ethylenedioxy)diphenol.

More preferable phenol compounds are phenol compounds having 6 to 27 carbon atoms consisting of carbon and hydrogen atoms and an oxygen atom of the phenolic hydroxyl group such as phenol, cresol, 3-isopropylphenol, 4-butylphenol, 2-cyclopentylphenol, 2,3-dimethylphenol, 2,3,6-trimethylphenol, 2,6-diisopropylphenol, 3,5-di-tert-butylphenol, 2,6-di-tert-butyl-4-methylphenol, 5-indanol, 5,6,7,8-tetrahydro-1-naphthol, naphthol, nonylphenol, 4-hydroxystyrene, 4-hydroxy-α-methylstyrene, 1,1'-bi-2-naphthol, catechol, resorcinol, hydroquinone, 2-methylresorcinol, 4-hexylresorcinol, 2,6-dihydroxynaphthalene, bis(4-hydroxyphenyl)methane, 2,2-bis(4-hydroxyphenyl)propane, 2,2-bis(4-hydroxy-3-methylphenyl)propane, 2,2'-biphenol, 4,4'-biphenol, phenylhydroquinone, 1,3,5-trihydroxybenzene, 2,4-di(4-hydroxyphenyl)-4-methyl-1-pentene, 2,4,6-tri(4-hydroxyphenyl)-2,6-dimethyl-3-hexene, 5-hydroxy-3-(4-hydroxyphenyl)-1,1,3-trimethyl-2,3-dihydroindene, 5-hydroxy-3-(4-hydroxyphenyl)-2,6-dimethyl-3-hexene and tri(4-hydroxyphenyl)methane; and halogenated phenols having 6 to 15 carbon atoms such as 3-fluorophenol, 2-trifluoromethylphenol, 4-chlorophenol, 2-bromophenol, 2,6-difluorophenol, 4-fluoro-2-methylphenol, 2,3,4-trichlorophenol, 2,2-bis(4-hydroxy-3,5-dichlorophenyl) propane, 2,2-bis(4-hydroxyphenyl)-1,1,1,2,2,2-hexafluoropropane and octafluoro-4,4'-biphenol.

In the process of this invention, an epoxy compound is reacted with a carboxylate, carboxylic anhydride, carbonate or phenol compound in the presence of a phosphine sulfide represented by formula (1). The carboxylate, carboxylic anhydride, carbonate or phenol compound can be used alone or in combination of two or more. In the latter case, a compound preferentially reacting with the epoxy compound may depend on reactivity of compounds used.

In the process of this invention, an epoxy compound may have both epoxy group and carboxylate, carboxylic anhydride, carbonate or phenolic hydroxyl group in one molecule. For such a compound, the reaction of this invention may intramolecularly occur. When such an epoxy compound is reacted with a separate carboxylic, caboxylic anhydride, carbonate or phenol compound, whether the epoxy group reacts intramolecularly or intermolecularly with the separate carboxylate, carboxylic anhydride, carbonate or phenol compound may depend on reactivity of the compounds used, and thus cannot be generally determined.

The reaction may be conducted in any procedure ensuring effective contact between a phosphine sulfide compound represented by formula (1), an epoxy compound and a carboxylate, carboxylic anhydride, carbonate or phenol compound. The reaction may be conducted in a continuous, batchwise or semi-batchwise system. It may be generally conducted by contacting the phosphine sulfide, the epoxy compound and the carboxylate, caboxylic anhydride, carbonate or phenol compound together; by adding the epoxy compound to a mixture comprising the phosphine sulfide and the carboxylate, carboxylic anhydride, carbonate or phenol compound; by adding the phosphine sulfide to a mixture comprising the epoxy compound and the carboxylate, carboxylic anhydride, carbonate or phenol compound; or by adding the carboxylate, carboxylic anhydride, carbonate or phenol compound to a mixture comprising the phosphine sulfide and the epoxy compound. A reactant may be added in one portion, intermittently or continuously.

The rate of the carboxylate, carboxylic anhydride, carbonate or phenol compound to the epoxy compound may be generally in the range of 0.5 to 1.5 moles, preferably 0.7 to 1.3 moles of the carboxylate, carboxylic anhydride, carbonate or phenolic hydroxyl group in the compound per mole of the epoxy group in the epoxy compound.

The amount of the phosphine sulfide represented by formula (1) is, but not limited to, generally below 0.5 moles, preferably $1 \times 10^{-5}$ to 0.1 moles, more preferably $1 \times 10^{-4}$ to $5 \times 10^{-2}$ moles per mole of the epoxy group in the epoxy compound in any type of reaction.

A reaction temperature may vary depending on various factors such as the types of reactants and the amount of a phosphine sulfide represented by formula (1) in any type of reaction, but is generally below 250° C., preferably 30 to 200° C. A reaction pressure may vary depending on the types of reactants in any type of reaction, but it is generally below 3.0 MPa (an absolute pressure; hereinafter, the same definition is used), preferably 0.01 to 1.5 MPa, more preferably 0.1 to 1.0 MPa. A reaction duration is generally within 48 hours, preferably 0.1 min to 24 hours, more preferably 0.6 min to 10 hours. The reaction may be, if necessary, conducted in an atmosphere of an inert gas such as nitrogen and argon.

In the process of this invention, a reaction may be, if necessary, conducted in the presence of a solvent. Solvents which may be used include aliphatic and alicyclic hydrocarbons such as n-pentane, n-hexane and cyclohexane; ethers such as dimethyl ether, diethyl ether, diisopropyl ether, dibutyl ether, tetrahydrofuran, 1,4-dioxane, ethylene glycol dimethyl ether, diethylene glycol dimethyl ether, anisole, o-dimethoxybenzene, ethyl phenyl ether, butyl phenyl ether and o-diethoxybenzene; aromatic hydrocarbons such as benzene, toluene, xylenes, ethylbenzene, cumene, mesitylene, tetralin, butylbenzene, p-cymene, diethylbenzene, diisopropylbenzene, triethylbenzene, cyclohexylbenzene, dipentylbenzene and dodecylbenzene; halogenated aromatic hydrocarbons such as chlorobenzene, o-dichlorobenzene, m-dichlorobenzene, 1,2,4-trichlorobenzene, bromobenzene, o-dibromobenzene, bromochlorobenzene, o-chlorotoluene, p-chlorotoluene, p-chloroethylbenzene and 1-chloronaphthalene; and aprotic polar solvents such as dimethyl sulfoxide, N,N-dimethylformamide, hexamethylphosphoramide and N,N'-dimethylimidazolidinone. Any other solvent may be used as long as it does not adversely affect the process of this invention. These solvents may be used alone or in combination of two or more.

An isolation procedure of a desired 1,2-dioxyethane derivative from a reaction solution may vary depending on the types of reactants used, the type of the desired 1,2-dioxyethane derivative and the type or the amount of a solvent used, but the desired 1,2-dioxyethane derivative may be generally isolated by a suitable isolation process such as distillation, recrystallization and column chromatography, from a reaction solution or a residue after evaporation when a solvent is used.

As described above, in the presence of a phosphine sulfide represented by formula (1), an epoxy compound may be reacted with a carboxylate, carboxylic anhydride, carbonate or phenol compound, to conveniently and effectively prepare a desired 1,2-dioxyethane derivative.

EXAMPLES

The first to fourth aspects of this invention will be more specifically described with Examples. It should be, however, noted that these examples are only illustrative, but not limitative in any manner.

The first and second aspects will be described.

Example 1

In a 100 cc flask in an atmosphere of nitrogen were placed 4.474 g of thiophosphoryl chloride (Aldrich)(26.41 mmol) and 45.24 g of o-dichlorobenzene (0.3078 mol) which had been dried on molecular sieves 3A to a moisture content of 10 ppm. While controlling an internal temperature at 40° C., to the stirred mixture was added dropwise 29.36 g of iminotris(dimethylamino)phosphorane (Fluka)(164.7 mmol) over 20 min., and then the mixture was maintained at 40° C. for 40 min. Then, the mixture was heated to 70° C. and reacted at the temperature for 20 hours, to provide a white suspension. The suspension was cooled to an ambient temperature, and then filtered to give a white solid.

The filtered white solid was dried. The solid was analyzed by mass spectrometry. There was observed a molecular ion peak at 179, which corresponds to the molecular weight of the cation moiety in aminotris(dimethylamino)phosphonium chloride, $\{[(CH_3)_2N]_3P^+(NH_2)Cl^-\}$.

The filtrate was washed with about 14 g of water three times. The o-dichlorobenzene phase was concentrated to dryness in vacuo to provide a dark blue solid (11.50 g; crude yield: 73%). Then, 9.64 g of the solid was added to 15.24 g of n-hexane, and the mixture was heated to 50° C. for completely dissolving the solid. The solution was cooled to 18° C. to precipitate crystal, which was then filtered and dried at 50° C./1 mmHg, to give 4.15 g of tris[tris(dimethylamino)phosphoranylideneamino]phosphine sulfide, a compound represented by formula (1) where R is methyl, as a white crystal (melting point: 90.0–92.5° C.). Elemental analysis data for the white crystal were;

Observed; C:36.77, H:9.47, N:28.28, P:21.01

Calculated; C:36.38, H:9.18, N:28.29, P:20.85

A portion of the white crystal was dissolved in DMSO-$d_6$ for $^{31}$P-NMR spectroscopy. The results are shown in FIG. 1, where a chemical shift for the phosphorous atom in tri-n-butyl phosphate which was used for quantitative analysis was set to 0.312 ppm. Under this condition, a chemical shift for the phosphorous atom in orthophosphoric acid usually used as a standard appears at 0.00 ppm.

As seen in FIG. 1, there are a quartet and a doublet at 17.1 and 12.2 ppm, respectively, which are derived from two different phosphorous atoms in tris[tris(dimethylamino)phosphoranylideneamino]phosphine sulfide and whose integrated intensity rate is 1:3. The quartet at 17.1 ppm corresponds to the single phosphorous atom bound to the sulfur atom at the center of the molecule. while the doublet at 12.2 ppm corresponds to three peripheral phosphorous atoms. The quartet at 17.1 ppm is observed because of coupling of the central phosphorous atom with the three peripheral phosphorous atoms while the doublet at 12.2 ppm is observed because of coupling of the peripheral phosphorous atoms with the central phosphorous atom.

Figure 2:
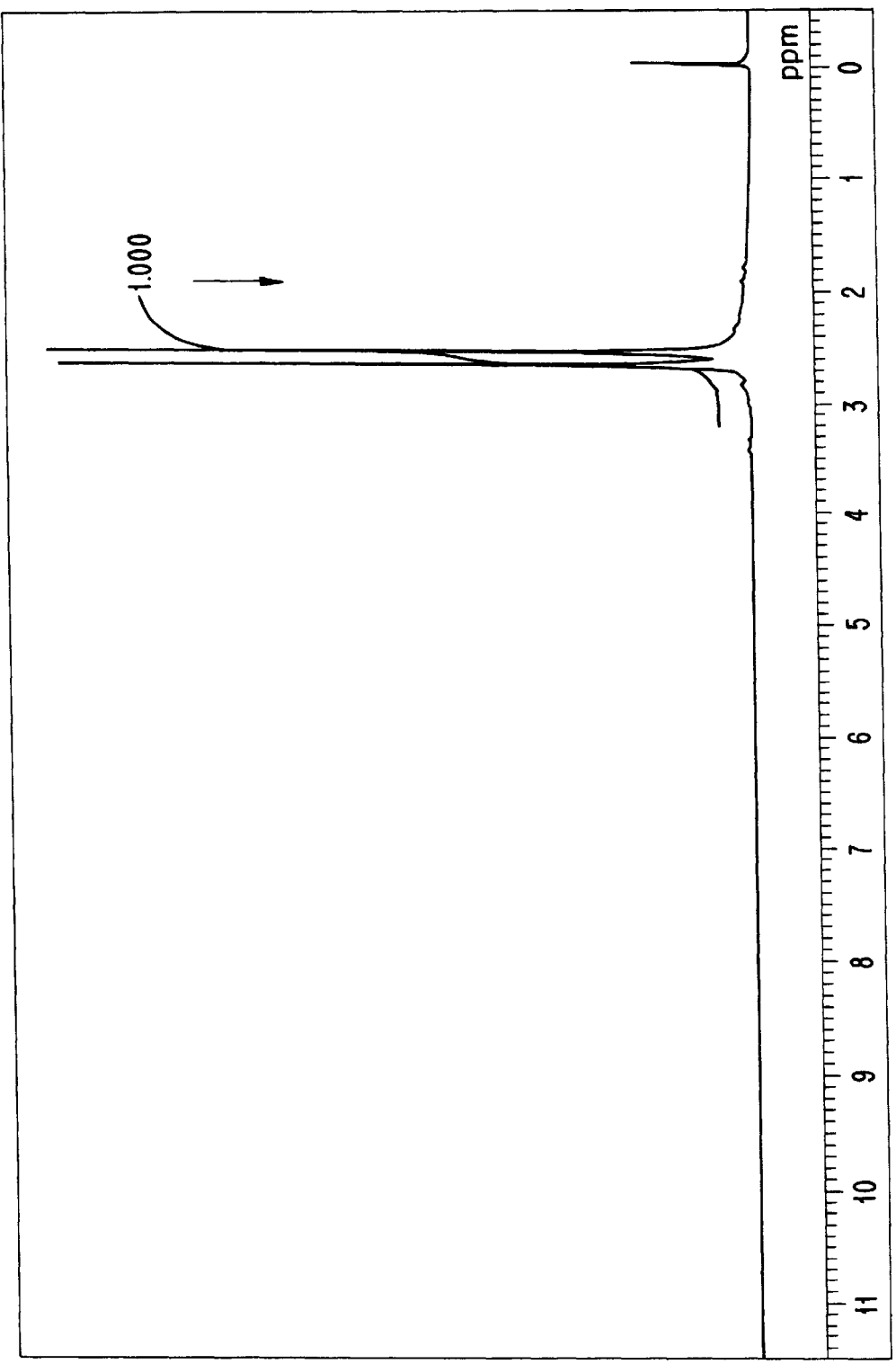
FIG. 2 shows a $^1$H-NMR spectrum for tris[tris (dimethylamino)phosphoranylideneamino]phosphine sulfide (solvent: DMSO-$d_6$).
Figure 3:
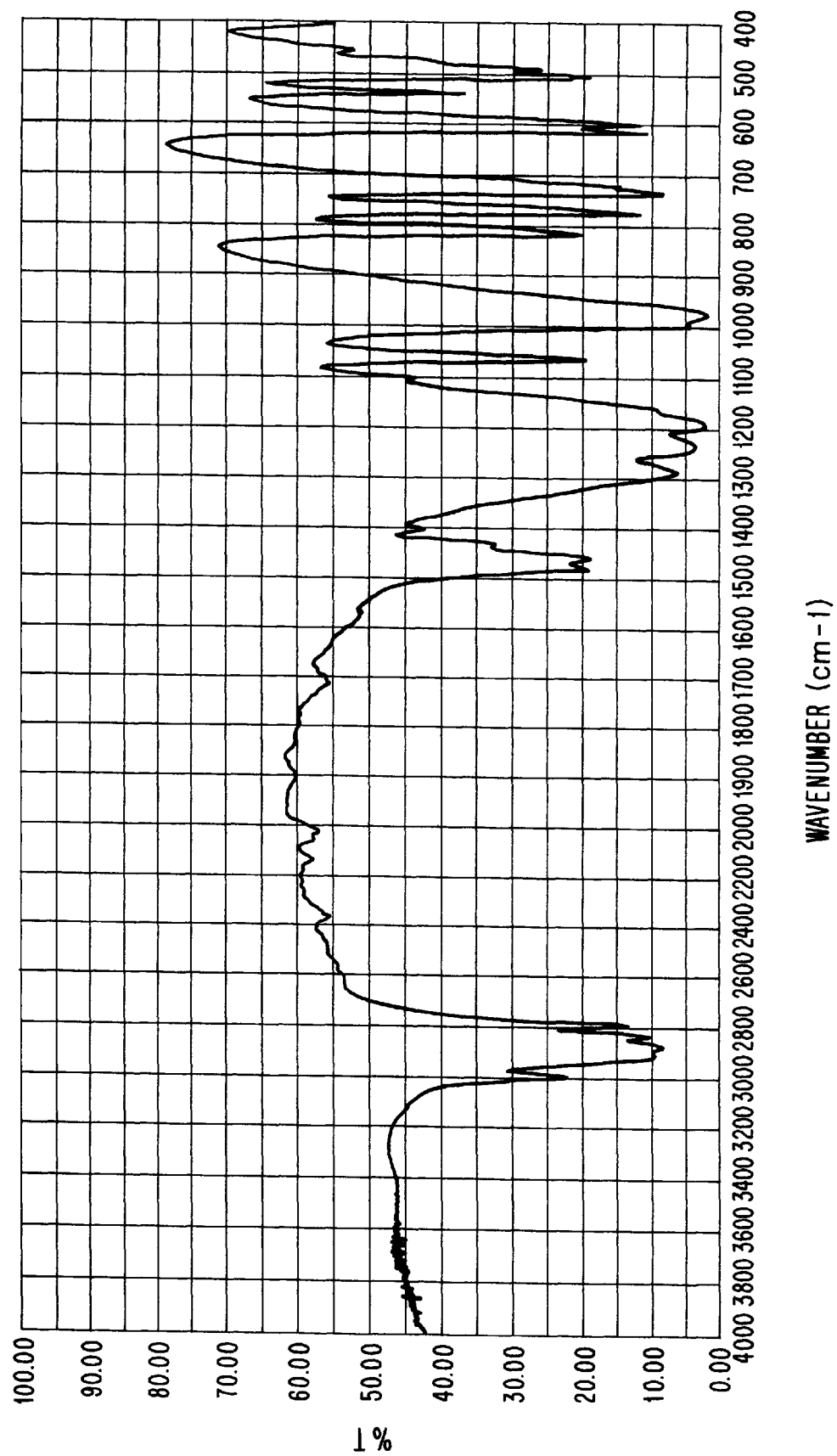
FIG. 3 shows an IR spectrum by a KBr pellet technique for tris[tris(dimethylamino)phosphoranylideneamino] phosphine sulfide (solvent: DMSO-$d_6$).

In addition, FIGS. 2 and 3 show a 1H-NMR spectrum for a DMSO-$d_6$ solution and an IR spectrum by a KBr pellet technique, respectively, of tris[tris(dimethylamino) phosphoranylideneamino]phosphine sulfide.

Preparation of poly(alkylene oxide)s as the third aspect of this invention will be described.

Example 2

In a 400 mL autoclave equipped with a temperature probe, a pressure gauge and an agitator were placed 1.03 g of tris[tris(dimethylamino)phosphoranylideneamino] phosphine sulfide (1.73 mmol), 13.1 g of glycerin (142 mmol) and 129 g of propylene oxide(2.22 mol). The atmosphere of the system was replaced with nitrogen. The mixture was heated to 80° C. and the temperature was kept for 17 hours, during which the maximum pressure was 0.3 MPa (an absolute pressure expressed in mega pascal; hereinafter, the same definition is used). At the end of the reaction, the pressure was 0.01 MPa. The residual pressure was purged while introducing nitrogen gas into the gaseous phase, and then the mixture was transferred to another vessel. The mixture was kept at 80° C. under a reduced pressure of 10 mmHg for 30 min. for removing volatiles. Then, nitrogen was introduced to the system to an ambient pressure and the mixture was cooled to an ambient temperature to give 125 g of polyoxypropylene triol containing tris[tris(dimethylamino)phosphoranylideneamino] phosphine sulfide as a transparent and odorless liquid.

Then, 33.2 g of the liquid was placed in a 400 mL autoclave equipped with a temperature probe, a pressure gauge, an agitator and an inlet tube for an alkylene oxide. After replacing the atmosphere of the system with nitrogen, the mixture was heated to 80° C., and then 197 g of propylene oxide (3.39 mol) was continuously introduced over 9 hours while controlling the reaction pressure below 0.4 MPa. After completion of the feed, the mixture was further reacted at 80° C. for 16 hours. At the end of the reaction, the pressure was reduced to 0.05 MPa. The residual pressure was purged while introducing nitrogen gas into the gaseous phase, and then the mixture was transferred to another vessel. The mixture was kept at 80° C. under a reduced pressure of 10 mmHg for 30 min. for removing volatiles.

Then, nitrogen was introduced to the system to an ambient pressure and the mixture was cooled to an ambient temperature to give 220 g of polyoxypropylene triol as a transparent and odorless liquid. A hydroxyl value for the polymer (the amount of terminal hydroxyl groups which is expressed by mg of equimolar amount of KOH with the hydroxy groups per 1 g of a polymer; KOH mg/g polymer) was 28.5, which provided an estimated number-average molecular weight of 5900. A molecular weight distribution (Mw/Mn) was 1.05 according to gel permeation chromatography using poly (ethylene oxide) as a standard.

Example 3

In a 400 mL polymerization reactor as described in Example 2 were placed 1.68 g of tris[tris(dimethylamino) phosphoranylideneamino]phosphine sulfide (2.82 mmol) and 29.1 g of dipropylene glycol (217 mmol). After replacing the atmosphere of the system with nitrogen, the mixture was heated to 90° C., and then 197 g of propylene oxide (3.39 mol) was continuously introduced over 7 hours while controlling the reaction pressure below 0.45 MPa. The mixture was further reacted at 90° C. for 12 hours. The pressure was reduced to 0.11 MPa. The residual pressure was purged while introducing nitrogen gas into the gaseous phase, and then the mixture was transferred to another vessel. The mixture was kept at 80° C. under a reduced pressure of 10 mmHg for 30 min for removing volatiles. Then, nitrogen was introduced to the system to an ambient pressure and the mixture was cooled to an ambient temperature to give 222 g of polyoxypropylene diol as a transparent and odorless liquid. Its hydroxyl value was 111, which provided an estimated number-average molecular weight of 1010.

Comparative Example 1

The procedure in Example 3 was repeated, except that tris[tris(dimethylamino)phosphoranylideneamino] phosphine sulfide was absent. No consumption of propylene oxide was observed. The weight of the content in the reaction vessel was 29.7 g, which was substantially equal to the weight of dipropylene glycol placed, and thus polyoxypropylene diol was not formed.

Example 4

The procedure in Example 3 was repeated, except that tris[tris(dimethylamino)phosphoranylideneamino] phosphine sulfide and dipropylene glycol were replaced with 88.2 g of polyoxypropylene triol obtained in Example 2 having a hydroxyl value of 28.5 and containing a catalyst component, and that 140 g of propylene oxide (2.41 mol) was introduced, to give 221 g of transparent and odorless polyoxypropylene triol whose hydroxyl value and number-average molecular weight were 11.9 and 14200, respectively.

Example 5

The procedure in Example 3 was repeated, except that tris[tris(dimethylamino)phosphoranylideneamino] phosphine sulfide and dipropylene glycol were replaced with 121 g of polyoxypropylene triol obtained in Example 2 having a hydroxyl value of 28.5 containing a catalyst component, and that 25.1 g of ethylene oxide (0.570 mol) was introduced over 1 hour in place of propylene oxide, and a reaction duration was 8 hours, to give 146 g of a block copolymer of transparent and odorless polyoxypropylene-polyoxyethylene triol whose hydroxyl value and number-average molecular weight were 23.7 and 7100, respectively.

Example 6

The procedure in Example 3 was repeated, except that the amount of tris[tris(dimethylamino) phosphoranylideneamino]phosphine sulfide was 0.277 g (0.466 mmol), dipropylene glycol was replaced with 31.1 g of polyoxypropylene triol having a hydroxyl value of 168 (number-average molecular weight: 1002)(MN-1000; Mitsui Chemical Inc.) industrially produced with a potassium hydroxide catalyst, and a reaction duration was 20 hours, to give 216 g of transparent and odorless polyoxypropylene triol whose hydroxyl value and number-average molecular weight were 24.4 and 6900, respectively.

Example 7

The procedure in Example 3 was repeated, except that dipropylene glycol was replaced with 6.95 g of methyl alcohol (217 mmol) and a reaction duration was 19 hours, to give 197 g of transparent and odorless polyoxypropylene monool whose hydroxyl value and number-average molecular weight were 63.0 and 890, respectively.

Example 8

The procedure in Example 3 was repeated, except that dipropylene glycol was replaced with 39.1 g of glucose (217 mmol), to give 227 g of transparent and odorless polyoxypropylene pentanol whose hydroxyl value and number-average molecular weight were 270 and 1040, respectively.

Example 9

The procedure in Example 3 was repeated, except that dipropylene glycol was replaced with 19.6 g of 1,4-butanediol (217 mmol), 244 g of 1,2-butylene oxide (3.39 mol) was introduced over 5 hours in place of propylene oxide while maintaining a pressure below 0.25 MPa, and a reaction duration was 20 hours, to give 251 g of transparent and odorless polyoxybutylene diol whose hydroxyl value and number-average molecular weight were 98.4 and 1140, respectively.

Example 10

The procedure in Example 3 was repeated, except that 300 g of styrene oxide (2.50 mol) was introduced over 5 hours in place of propylene oxide while maintaining a pressure below 0.15 MPa, and a reaction duration was 15 hours, to give 306 g of transparent and odorless polyoxystyrene diol whose hydroxyl value and number-average molecular weight were 81.3 and 1380, respectively.

Example 11

The procedure in Example 3 was repeated, except that dipropylene glycol was replaced with 13.0 g of ethylenediamine (217 mmol), to give 200 g of transparent and odorless polyoxypropylene tetraol whose hydroxyl value and number-average molecular weight were 247 and 910, respectively.

Example 12

The procedure in Example 3 was repeated, except that dipropylene glycol was replaced with 18.7 g of piperazine (217 mmol) and a reaction duration was 8 hours, to give 211 g of transparent and odorless polyoxypropylene diol whose hydroxyl value and number-average molecular weight were 117 and 960, respectively.

Example 13

The procedure in Example 3 was repeated, except that dipropylene glycol was replaced with 15.4 g of pyrrolidine (217 mmol) and a reaction duration was 10 hours, to give 206 g of transparent and odorless polyoxypropylene monool whose hydroxyl value and number-average molecular weight were 59.7 and 940, respectively.

Preparation of 1,2-dioxyethane derivatives as the fourth aspect of this invention will be described.

Example 14

In a 100 mL pear-shaped flask were precisely weighed 0.595 g of tris[tris(dimethylamino) phosphoranylideneamino]phosphine sulfide (1.00 mmol) and 14.3 g of phenyl acetate (105 mmol). To the mixture warmed to 90° C. was added dropwise 15.0 g of phenyl glycidyl ether (100 mmol) over 10 min. After addition, the mixture was stirred at the same temperature for 5 hours, and cooled to room temperature over about 10 min. A small portion of the reaction mixture was quantitatively analyzed by gas chromatography using 1,3,5-trichlorobenzene as an internal standard, indicating that the starting phenyl glycidyl ether had been almost completely consumed to form desired 1,3-diphenoxy-2-propyl acetate in an yield of 98% based on phenyl glycidyl ether. In brief, the reaction was almost quantitatively proceeded.

The reaction mixture was directly subjected to column chromatography to give 27.2 g of 1,3-diphenoxy-2-propyl acetate as a colorless liquid whose analytical data were identical to those for a reference standard. The catalyst activity (a molar amount of a desired product per one mole of a catalyst in a unit time, in TON/h; hereinafter, the same definition is used) of tris [tris(dimethylamino) phosphoranylideneamino]phosphine sulfide was 20 TON/h, which was surprisingly about 13, 6 or 7 times as large as that given by N-methylimidazole, tetrabutylammonium chloride or potassium tert-butoxide in Comparative Example 3, 4 or 5, respectively. Thus, phenyl glycidyl ether and phenyl acetate are reacted to provide 1,3-diphenoxy-2-propyl acetate, namely a 1,2-dioxyethane derivative in a markedly higher catalytic activity and a higher yield.

Comparative Example 2

The procedure in Example 14 was repeated, except that tris[tris(dimethylamino)phosphoranylideneamino] phosphine sulfide was absent. An yield of 1,3-diphenoxy-2-propyl acetate was 1%.

Comparative Example 3

The procedure in Example 14 was repeated, except that tris[tris(dimethylamino)phosphoranylideneamino] phosphine sulfide was replaced with an equal molar amount of N-methylimidazole. An yield of 1,3-diphenoxy-2-propyl acetate was 8%. A catalytic activity was as low as 1.5 TON/h.

Comparative Example 4

The procedure in Example 14 was repeated, except that tris[tris(dimethylamino)phosphoranylideneamino] phosphine sulfide was replaced with an equal molar amount of tetrabutylammonium chloride. An yield of 1,3-diphenoxy-2-propyl acetate was 18%. A catalytic activity was as low as 3.6 TON/h.

Comparative Example 5

The procedure in Example 14 was repeated, except that tris[tris(dimethylamino)phosphoranylideneamino] phosphine sulfide was replaced with an equal molar amount of potassium tert-butoxide. An yield of 1,3-diphenoxy-2-propyl acetate was 15%. A catalytic activity was as low as 3.0 TON/h.

Example 15

In a 200 mL autoclave were placed precisely weighed ethyl acetate (37.0 g, 420 mmol) and tris[tris (dimethylamino)phosphoranylideneamino]phosphine sulfide (0.595 g, 1.00 mmol). To the mixture warmed to 100° C. was intermittently introduced 23.2 g of propylene oxide (400 mmol) for maintaining the reaction pressure at 0.4 MPa while heating the system at the same temperature for 13 hours. The mixture was cooled to an ambient temperature over about 30 min. A small portion of the reaction mixture was quantitatively analyzed by gas chromatography, indicating that the desired 2-acetoxy-1-ethoxypropane was produced in an yield of 90%. After distillation of the reaction mixture, 47.3 g of 2-acetoxy-1-ethoxypropane was obtained.

Example 16

The procedure in Example 15 was repeated, except that ethyl acetate was replaced with an equal molar amount of methyl benzoate and propylene oxide was replaced with an equal molar amount of ethylene oxide. An yield of the desired 2-methoxyethyl benzoate was 89%.

Example 17

The procedure in Example 14 was repeated, except that phenyl glycidyl ether was replaced with a half molar amount of 2,2-bis(4-glycidyloxyphenyl)propane. An yield of the desired 2,2-bis[4-(2-acetoxy-3-phenoxypropoxy)phenyl] propane was 92%.

Example 18

The procedure in Example 14 was repeated, except that phenyl acetate was replaced with an equal molar amount of phenyl benzoate and phenyl glycidyl ether was replaced with an equal molar amount of 4-phenoxyphenyl glycidyl ether. An yield of the desired 1-phenoxy-3-(4-phenoxyphenoxy)-2-propyl benzoate was 99%.

Example 19

The procedure in Example 14 was repeated, except that phenyl acetate was replaced with an equal molar amount of 4-methoxyphenyl 5-methoxypentanoate and phenyl glycidyl ether was replaced with an equal molar amount of glycidyl acetate. An yield of the desired 1-acetoxy-3-(4-methoxyphenoxy)-2-propyl 5-methoxypentanoate was 92%.

Example 20

The procedure in Example 15 was repeated, except that ethyl acetate was replaced with an equal molar amount of methyl 4-phenoxybenzoate. An yield of the desired 1-methoxy-2-propyl 4-phenoxybenzoate was 84%.

Example 21

The procedure in Example 14 was repeated, except that phenyl acetate was replaced with an equal molar amount of acetic anhydride, phenyl glycidyl ether was replaced with an equal molar amount of styrene oxide, and a reaction temperature was 85° C. An yield of the desired 1,2-diacetoxyethylbenzene was 97%.

Example 22

The procedure in Example 14 was repeated, except that phenyl acetate was replaced with an equal molar amount of benzoic anhydride, phenyl glycidyl ether was replaced with an equal molar amount of 4-methoxycarbonylstyrene oxide, and a reaction temperature was 85° C. An yield of the desired 1-(1,2-dibenzoyloxyethyl)-4-methoxycarbonylbenzene was 94%.

Example 23

The procedure in Example 14 was repeated, except that phenyl acetate was replaced with an equal molar amount of dimethyl carbonate and phenyl glycidyl ether was replaced with an equal molar amount of 4-methoxystyrene oxide. An yield of the desired 1-(1-methoxy-2-methoxycarbonyloxyethyl)-4-methoxybenzene was 82%.

Example 24

The procedure in Example 14 was repeated, except that phenyl acetate was replaced with an equal molar amount of diphenyl carbonate. An yield of the desired 1,3-diphenoxy-2-phenoxycarbonyloxypropane was 86%.

Example 25

The procedure in Example 14 was repeated, except that phenyl acetate was replaced with an equal molar amount of 2-methoxyethyl 4-methoxyphenyl carbonate. An yield of the desired 1-phenoxy-3-(4-methoxyphenoxy)-2-(2-methoxyethoxycarbonyloxy)propane was 96%.

Example 26

The procedure in Example 14 was repeated, except that phenyl acetate was replaced with an equal molar amount of phenol. An yield of the desired 1,3-diphenoxy-2-propanol was 99%.

Example 27

The procedure in Example 14 was repeated, except that phenyl acetate was replaced with a half molar amount of 2,2-bis(4-hydroxyphenyl)propane. An yield of the desired 2,2-bis[4-(2-hydroxy-3-phenoxypropoxy)phenyl]propane was 95%.

Example 28

The procedure in Example 14 was repeated, except that phenyl acetate was replaced with an equal molar amount of 4-chlorophenol. An yield of the desired 1-(4-chlorophenoxy)-3-phenoxy-2-propanol was 97%.

Example 29

The procedure in Example 14 was repeated, except that phenyl acetate was replaced with an equal molar amount of 3-phenoxyphenol. An yield of the desired 1-(3-phenoxyphenoxy)-3-phenoxy-2-propanol was 93%.

A phosphine sulfide represented by formula (1) of this invention is a novel compound which is basic and soluble in an organic solvent, does not have a problem in preparation or handling and exhibits catalytic activity as a basic compound.

According to this invention, the phosphine sulfide having such properties can be conveniently prepared.

According to this invention, a poly(alkylene oxide) can be effectively prepared by polymerizing an alkylene oxide without any treatment prior to polymerization and without generating residual amine odor. Furthermore, a 1,2-dioxyethane derivative may be effectively prepared by reacting an epoxy compound with a carboxylate, carboxylic anhydride, carbonate or phenol compound.

What is claimed is:

1. A phosphine sulfide represented by formula (1):

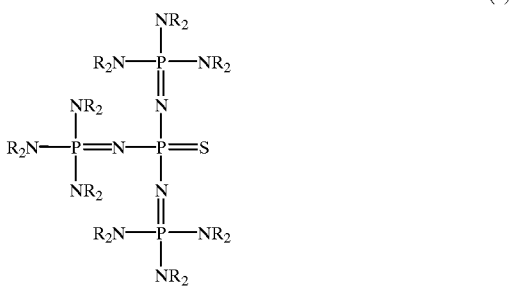

wherein R is the same or different and each represents a hydrocarbon group having 1 to 10 carbon atoms.

2. A phosphine sulfide as claimed in claim 1 wherein R in formula (1) is methyl.

3. A process for manufacturing a phosphine sulfide represented by formula (1) as claimed in claim 1, comprising reacting one molecule of thiophosphoryl chloride with three molecules of a phosphorane represented by formula (2):

wherein R is the same or different and each represents a hydrocarbon group having 1 to 10 carbon atoms.

4. A process as claimed in claim 3 wherein R in formula (2) is methyl.

5. A process for manufacturing a poly(alkylene oxide), comprising polymerizing an alkylene oxide in the presence of a phosphine sulfide represented by formula (1) or of the phosphine sulfide and an active hydrogen compound selected from water and organic compounds having a partial structure of —OH or —NH— wherein formula (1) is as follows:

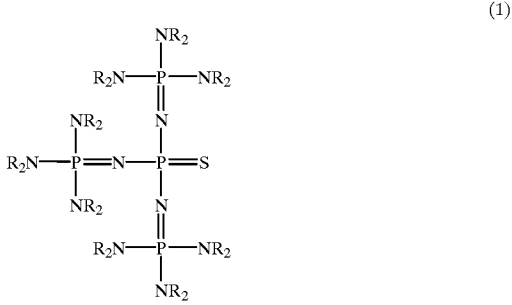

wherein R is the same or different and each represents a hydrocarbon group having 1 to 10 carbon atoms.

6. A process as claimed in claim 5 wherein the alkylene oxide is selected from the group consisting of ethylene oxide, propylene oxide, 1,2-butylene oxide or styrene oxide.

7. A process for manufacturing a 1,2-dioxyethane derivative having a partial structure represented by formula (3), (4), (5) or (6);

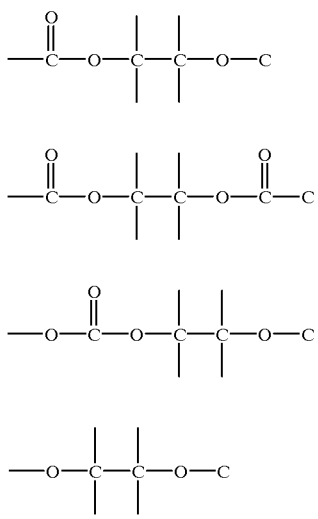

(3)
(4)
(5)
(6)

wherein a carbon atom C— or —C attached to a carbonyl group or an oxygen atom belongs to an aliphatic, alicyclic or aromatic hydrocarbon, comprising reacting an epoxy compound with a carboxylate, carboxylic anhydride, carbonate or phenol compound, respectively, in the presence of a phosphine sulfide represented by formula (1)

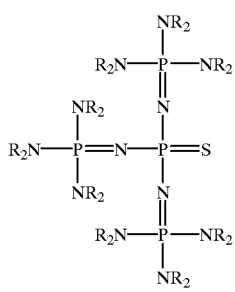

(1)

wherein R is the same or different and each represents a hydrocarbon group having 1 to 10 carbon atoms.

8. A process as claimed in claim 7 wherein the epoxy compound is (a) an aliphatic or aromatic epoxy compound consisting of carbon and hydrogen atoms and an oxygen atom of the epoxy group; (b) an aliphatic or aromatic epoxy compound having an ether bond; or (c) an aliphatic or aromatic epoxy compound having an ester bond.

9. A process as claimed in claim 7 wherein the carboxylate is (a) an aliphatic or aromatic carboxylate consisting of carbon and hydrogen atoms and oxygen atoms of the ester bond; or (b) an aliphatic or aromatic carboxylate having an ether bond.

10. A process as claimed in claim 7 wherein the carboxylic anhydride is an aliphatic or aromatic carboxylic anhydride consisting of carbon and hydrogen atoms and oxygen atoms of the carboxylic anhydride group.

11. A process as claimed in claim 7 wherein the carbonate is (a) an aliphatic or aromatic carbonate consisting of carbon and hydrogen atoms and oxygen atoms of the carbonate group; or (b) an aliphatic or aromatic carbonate having an ether bond.

12. A process as claimed in claim 7 wherein the phenol compound is (a) a phenol compound consisting of carbon and hydrogen atoms and an oxygen atom of the phenolic hydroxyl group; (b) a halogenated phenol compound; or (c) a phenol compound having an ether bond.

13. A process as claimed in claim 12 wherein R in formula (1) is methyl.

14. A process as claimed in claim 5 wherein R in formula (I) is methyl.

15. A process as claimed in claim 6 wherein R in formula (I) is methyl.

16. A process as claimed in claim 7 wherein R in formula (I) is methyl.

17. A process as claimed in claim 8 wherein R in formula (I) is methyl.

18. A process as claimed in claim 9 wherein R in formula (I) is methyl.

19. A process as claimed in claim 10 wherein R in formula (I) is methyl.

20. A process as claimed in claim 11 wherein R in formula (I) is methyl.

* * * * *